US006207700B1

(12) United States Patent
Kalgutkar et al.

(10) Patent No.: US 6,207,700 B1
(45) Date of Patent: Mar. 27, 2001

(54) AMIDE DERIVATIVES FOR ANTIANGIOGENIC AND/OR ANTITUMORIGENIC USE

(75) Inventors: Amit S. Kalgutkar; Lawrence J. Marnett, both of Nashville, TN (US)

(73) Assignee: Vanderbilt University, Nashville, TN (US)

(*) Notice: Subject to any disclaimer, the term of this patent is extended or adjusted under 35 U.S.C. 154(b) by 0 days.

(21) Appl. No.: 09/226,693

(22) Filed: Jan. 7, 1999

(51) Int. Cl.[7] ............................. A01N 43/38; A61K 31/40
(52) U.S. Cl. ................................................. 514/420
(58) Field of Search ............................................. 514/420

(56) References Cited

U.S. PATENT DOCUMENTS

| | | | |
|---|---|---|---|
| 3,161,654 | 12/1964 | Shen | 260/319 |
| 3,285,908 | 11/1966 | Shen | 260/211 |
| 3,336,194 | 8/1967 | Shen | 167/65 |
| 3,654,349 | 4/1972 | Shen et al. | 260/515 M |
| 3,725,548 | 4/1973 | Shen et al. | 424/303 |
| 4,229,447 | 10/1980 | Porter | 424/244 |
| 4,412,994 | 11/1983 | Sloan et al. | 424/248.53 |
| 4,851,426 | 7/1989 | Ladkani et al. | 514/420 |
| 5,016,652 | 5/1991 | Rose et al. | 131/270 |
| 5,032,588 | 7/1991 | Brooks et al. | 514/224.8 |
| 5,436,265 | 7/1995 | Black et al. | 514/420 |
| 5,504,086 | 4/1996 | Ellinwood, Jr. et al. | 514/252 |
| 5,510,368 * | 4/1996 | Lau et al. | 514/419 |
| 5,607,966 | 3/1997 | Hellberg et al. | 514/458 |
| 5,681,964 | 10/1997 | Ashton et al. | 548/491 |
| 5,811,438 | 9/1998 | Hellberg et al. | 514/458 |
| 6,048,850 | 4/2000 | Young et al. | |

FOREIGN PATENT DOCUMENTS

| | | |
|---|---|---|
| 190749 | 12/1981 | (CS) . |
| 2735537 | 2/1979 | (DE) . |
| 2926472 | 1/1981 | (DE) . |
| 3145465 | 5/1983 | (DE) . |
| 3235850 | 8/1983 | (DE) . |
| 3206885 | 9/1983 | (DE) . |
| 51278 | 5/1982 | (EP) . |
| 144845 | 6/1985 | (EP) . |
| 327766 | 8/1989 | (EP) . |
| 335164 | 10/1989 | (EP) . |
| 335545 | 10/1989 | (EP) . |
| 342682 | 11/1989 | (EP) . |
| 432545 | 11/1976 | (ES) . |
| 2392008 | 12/1978 | (FR) . |
| 54-090174 | 7/1979 | (JP) . |
| 58-201763 | 11/1983 | (JP) . |
| 59-161358 | 9/1984 | (JP) . |
| 61-060649 | 3/1986 | (JP) . |
| 63-196598 | 8/1988 | (JP) . |
| 63275593 | 11/1988 | (JP) . |
| 8105139 | 6/1982 | (NL) . |
| 95/04030 | 2/1995 | (WO) . |
| 95/20567 | 8/1995 | (WO) . |

OTHER PUBLICATIONS

Fisnerova et al., "Pharmacologically Interesting Indomethacin Derivates," Heterocycles, p. 373 (1978), and only Abstract in English.

Diago–Meseguer et al., "A New Reagent for Activating Carboxyl Groups; Preparation and Reactions of N,N–Bis [2–oxo–3–oxaxolidinyl]phosphorodiamidic Chloride", Synthesis, pp. 547–551 (Jul., 1980).

Linari et al., "Substituted Anilides of 1–(p–Chlorobenzoyl)–5–methoxy–2–methyl–indole–3–acetic Acid", vol. 23, No. 1, Arzneim–Foprsch. (Drug Res. ), pp. 89–91 (1973).

Tammara et al., "Synthesis and Evaluation of Morpholinoalkyl Ester Prodrugs of Indomethacin and Naproxen", vol. 10, No. 8, Pharmaceutical Research, pp. 1191–1199 (1993).

Katori et al., "Induction of Prostglandin H Synthase–2 in Rat Carrageenin–induced Pleurisy and Effect of a Selective Cox–2 Inhibitor", vol. 23, Advances in Prostaglandin, Thromboxane, and Leukotriene Research, pp. 345–347, (1995).

DeWitt et al., "Primary Structure of Prostaglandin G/H Synthase from Sheep Vesicular Gland Determined from the Complementary DNA Sequence", vol. 85, Proc. Natl. Acad. Sci. USA, pp. 1412–1416 (Mar., 1988).

Smith et al., "Prostaglandin Endoperoxide H Synthases (Cyclooxygenases)–1 and –2", vol. 271, No. 52, The Journal of Biological Chemistry, pp. 33157–33160 (Dec. 27, 1996).

Yokoyama et al., "Cloning of Human Gene Encoding Prostaglandin Endoperoxide Synthase and Primary Structure of the Enzyme", vol. 165, No. 2, Biochemical and Biophysical Research Communications, pp. 888–894, (Dec. 15, 1989).

Hla et al., "Human Cyclooxygenase–2 cDNA", vol. 89, Proc Natl. Acad. USA, pp. 7384–7388, (Aug., 1992).

Kujubu et al., "TIS10, a Phorbol Ester Tumor Promoter–inducible mRNA from Swiss 3T3 Cells, Encodes a Novel Prostaglandin Synthase/Cyclooxygenase Homologue", The Journal of Biological Chemistry, vol. 266, No. 20, pp. 12866–12872, (Jul. 15, 1991).

Allison et al., "Gastrointestinal Damage Associated with the Use of Nonsteroidal Antiinflammatory Drugs", vol. 327, No. 11, The New England Journal of Medicine, pp. 749–754, (Sep. 10, 1992).

Lee et al., "Selective Expression of Mitogen–inducible Cyclooxygenase in Macrophages Stimulated with Lipopolysaccharide", vol. 267, The Journal of Biological Chemistry, pp. 25934–25938, (Dec. 25, 1992).

(List continued on next page.)

Primary Examiner—Dwayne C. Jones
(74) Attorney, Agent, or Firm—Jenkins & Wilson, P.A.

(57) ABSTRACT

A method of treating animals having cancer by administration of secondary amide derivatives of various COOH-containing drugs, such as COOH-containing NSAIDs, for instance, indomethacin.

11 Claims, No Drawings

OTHER PUBLICATIONS

Penning et al., "Synthesis and Biological Evaluation of the 1,5–Diarylpyrazxole Class of Cyclooxygenase–2 Inhibitors: Identification of 4–[5(4–Methylphenyl)–3–(trifluoromethyl)–1H–pyrazol–1–yl]benzenesulfonamide (SC–58635, Celecoxib)", vol. 40, *J. Med Chem.*, pp. 1347–1365, (1997).

Gans et al., "Anti–Inflammatroy and Safety Profile of DuP 697, a Novel Orally Effective Prostaglandin Synthesis Inhibitor", vol. 254, No. 1, *The Journal of Pharmacology and Experimental Therapeutics*, pp. 180–187, (1990).

Khanna et al., "1,2–Diarylimidazoles a Potent, Cyclooxygenase–2 Selective, and Orally Active Antiinflammatory Agents", vol. 40, No. 11, *Journal of Medicinal Chemistry*, pp. 1634–1647, (1997).

Vane et al., "Inducible Isoforms of Cyclooxygenase and Nitric–Oxide Synthase in Inflammation", vol. 91, *Proc. Natl. Acad. Sci. USA*, pp. 2046–2050 (Mar., 1994).

Masferrer et al., "Selective Inhibition of Inducible Cyclooxygenase 2 In Vivo is Antiinflammatory and Nonulcerogenic", vol. 91, *Proc. Natl. Acad. Sci. USA*, pp. 3228–3232 (Apr., 1994).

O'Sullivan et al., "Lipopolysaccharide–induced Expression of Prostaglandin H Synthase–2 in Alveolar Macrophages is Inhibited by Dexamethasone but not by Aspirin", vol. 191, No. 3, *Biochemical and Biophysical Research Communications*, pp. 1294–1300 (Mar. 31, 1993).

Kennedy et al., "Cloning and Expression of Rat Prostaglandin Endoperoxide Synthase (Cyclooxygenase)–2 cDNA", vol. 197, No. 2, *Biochemical and Biophysical Research Communications*, pp. 494–500 (Dec. 15, 1993).

Khanna et al., "1,2–Diarylpyrroles as Potent and Selective Inhibitors of Cyclooxygenase–2", vol. 40, No. 11 *Journal of Medicinal Chemistry*, pp. 1619–1633, (1997).

Meade et al., "Differential Inhibition of Prostaglandin Endoperoxide Synthase (Cyclooxygenase) Isozymes by Aspirin and Other Non–steroidal Anti–inflammatory Drugs", vol. 238, No. 9, *The Journal of Biological Chemistry*, pp. 6610–6614 (Mar. 25, 1993).

Futaki et al., "NS–398, a New Anti–inflammatory Agent, Selectively Inhibits Prostaglandin G/H Synthase/cyclooxygenase (COX–2) Activity In Vitro", vol. 47, *Pharmaceutical Research*, pp. 55–59 (Jan., 1994).

Li et al., "Novel Terphenyls as Selective Cyclooxygenase–2 Inhibitors and Orally Active Anti–Inflammatory Agents", vol. 39, *J. Med. Chem.*, pp. 1846–1856 (1996).

Riendeau et al., "Biochemical and Pharmacological Profile of a Tetrasubstituted Furanone as a Highly Selective COX–2 Inhibitor", vol. 121, *British Journal of Pharmacology*, pp. 105–117 (1997).

Tsuji et al., "Studies on Anti–inflammatory Agents. IV. Synthesis and Pharmacological Properties of 1,5–Diarylpyrazoles and Related Derivatives", vol. 45, No. 6, *Chem,. Pharm. Bull.*, pp. 987–995, (Jun., 1997).

Thérien et al., "Synthesis and Biological Evaluation of 5,6–Diarylimidazo[2.1–b]Thiazole as Selective COX–2 Inhibitors", vol. 7, No. 1, *Bioorganic & Medicinal Chemistry Letters*, pp. 47–52, (1997.

Roy et al., "A New Series of Selective COX–2 Inhibitors: 5,6–Diarylthiazolo[3,2–b][1,2,4]Triazoles", vol. 7, No. 1, *Bioorganic & Medicinal Chemistry Letters*, pp. 57–62, (1997).

Li et al., "1,2–Diarylcyclopentenes as Selective Cyclooxygenase–2 Inhibitors and Orally Active Anti–Inflammatory Agents", vol. 38, *J. Med. Chem.*, pp. 4570–4578, (1995).

Reitz et al., "Novel 1,2–Diarylcyclopentenes are Selective, Potent, and Orally Active Cyclooxygenase Inhibitors", vol. 5, *Med. Chem. Res.*, pp. 351–363, (1995).

Li et al., "Cyclooxygenase–2 Inhibitors. Synthesis and Pharmacological Activities of 5–Methanesulfonamido–1–indanone Derivatives", vol. 38, *Journal of Medicinal Chemistry*, pp. 4897–4905, (1995).

Downing et al., "Structural Requirements of Acetylenic Fatty Acids for Inhibition of Soybean Lipoxygenase and Prostaglandin Synthetase", vol. 280, *Biochem. Biophys. Acta.*, pp. 343–347, (1972).

Downing et al., "Enzyme Inhibition by Acetylenic Compounds", vol. 40, No. 1 *Biochemical and Biophysical Communications*, pp. 218–223, (1970).

Devane et al., "Isolation and Structure of a Brain Constituent that Binds to the Cannabinoid Receptor", vol. 258, *Science*, pp. 1946–1949, (Dec. 18, 1992).

Ramesha, "Human and Rat Cyclooxygenases are Pharmacologically Distinct", *Eicosanoids and Other Bioactive Lipids in Cancer Inflammation and Radiation Injury 3*, pp. 67–71, (1997).

Luong et al., "The Structure of Human Cyclooxygenase–2: Conservation and Flexibility of the NSAID Binding Site", vol. 3, *Nature Structural Biology*, pp. 927–933, (1996).

Yu et al., "Synthesis of Prostaglandin $E_2$ Ethanolamide from Anandamide by Cyclooxygenase–2", vol. 272, No. 34 *Journal of Biological Chemistry*, pp. 21181–21186, (Aug. 22, 1997).

Prasit et al., "L–745,337: A Selective Cyclooxygenase–2 inhibitor", vol. 5, *Med. Chem. Res.*, pp. 364–374, (1995).

Pal et al., "7–Oxabicycloheptylprostanoic Acids: Potent, Time–Dependent Cyclooxygenase Inhibitors that Induce a Conformational Change in the Prostaglandin Endoperoxide Synthase Protein", vol. 35, No. 12 *Journal of Medicinal Chemistry*, pp. 2340–2342, (1992).

Kalgutkar et al., "Aspirin–like Molecules that Covalently Inactivate Cyclooxygenase–2", vol. 280, *Science*, pp. 1268–1270, (May 22, 1998).

Flynn et al., "Nonsteroidal Antiinflammatory Drug Hydroxamic Acids. Dual Inhibitors of Both Cyclooxygenase and 5–Lipoxygenase", vol. 33, *J. Med. Chem.*, pp. 2070–2072, (1990).

Kolasa et al., "Nonsteroidal Anti–Inflammatory Drugs as Scaffolds for the Design of 5–Lipoxygenase Inhibitors,", vol. 40, *J. Med. Chem.*, pp. 819–924, (1997).

Black et al., "From Indomethacin to a Selective COX–2 Inhibitor: Development of Indolalkanoic Acids as Potent and Selective Cyclooxygenase–2 Inhibitors", vol. 6, No. 6, *Bioorganic & Medicinal Chemistry Letters*, pp. 725–730, (1996).

Chan et al., "Pharmacology of a Selective Cyclooxygenase–2 Inhibitor, L–745,337: A Novel Nonsteroidal Anti–inflammatory Agent with an Ulcerogenic Sparing Effect in Rat and Nonhuman Primate Stomach", vol. 274, No. 3, *The Journal of Pharmacology and Experimental Therapeutics*, pp. 1531–1537, (1995).

Nakamura et al., "Studies on Antiinflammatory Agents II. Synthesis and Pharmacological Properties of 2'–(Phenylthio)methanesulfonanilides and Related Derivatives", vol. 41, No. 5, *Chem. Pharm. Bull.*, pp. 894–906, (1993).

Tanaka et al., "Pharmacological Studies of the New Antiinflammatory Agent 3–Formylamino–7–methylsulfonylamino–6–phenoxy–4H–1–benzopyran–4–one", vol. 42(II), No. 7, *Arzneim–Forsch/Drug Res.*, pp. 935–944, (1992).

Boltze et al., "Chemical Structure and Anti–inflammatory Activity in the Group of Substituted Indole–3–acetic Acids", vol. 30 (II), No. 8a, *Arzneim–Forsch/Drug Res.*, pp. 1314–1325, (1980).

Graedon et al., "Pills Promise Relief Without Ulcers", published in *The News and Observer*, p. 8D, (Sep. 13, 1998).

Ogiso et al., "Pharmacokinetics of Indomethacin Ester Prodrugs: Gastrointestinal and Hepatic Toxicity and Hydrolytic Capacity of Various Tissues in Rats", vol. 19, No. 9, *Biol. Pharm. Bull.*, pp. 1178–1183 (Sep., 1996).

Sauvaire et al., "Pharmacological Activity and Toxicity of Apyramide: Comparison with Non–steroidal Anti–inflammatory Agents", vol. 13, No. 5, *Drugs Exp. Clin. Res.*, pp. 247–252, (1987).

Weisenberg–Boettcher et al., "The Pharmacological Profile of CGP 28238, a Novel Highly Potent Anti–inflammatory Compound", vol. 15, No. 11–12, *Drugs Exp. Clin. Res.*, pp. 501–509, (1989).

Davaran et al., "Acrylic Type Polymers Containing Ibuprofen and Indomethacin with Disfunctional Spacer Group; Synthesis and Hydrolysis", vol. 47, No. 1, *J. Controlled Release*, pp. 41–49, (1997).

Kappe et al., "Non–steroidal Antiinflammatory Agents. V. Basic Esters of Indomethacin", vol. 332, No. 4, *J. Prakt Chem.*, pp. 475–478, (1990).

Kwapiszewski et al., "Synthesis of N–[1–(p–chlorobenzoyl)–5–methoxy–2–methyl–3–indoleacetyl] Amino Acids and their Esters", vol. 39, No. 5–6, *Acto. Pol. Pharm.*, pp. 327–336, (1982).

Otis et al., "Synthesis and Pharmological Evaluation of Amide Derivatives of Nonsteroidal Anti–inflammatory Drugs", vol. 1, No. 3, *Inflammopharmacology*, pp. 201–212, (1992).

Rojo et al., "Variable Effects of Indomethacin and Four Related Compounds on Lymphocyte Blastogenesis and Cell–mediated Cytotoxicity", vol. 19, No. 9, *Int. J. Clin. Pharmocol., Ther. Toxicol.*, pp. 420–424, (1981).

Svoboda et al., "Potential Anti–inflammatory Agents Based on Indomethacin Esters", vol. 40, No. 2, *Cesk. Farm.*, pp. 71–74, (1991).

Phelan et al., "Improved Delivery Through Biological Membranes. XXXVII. Synthesis and Stability of Novel Redox Derivatives of Naproxen and Indomethacin", vol. 6, No. 8, *Pharm. Res.*, pp. 667–676, (1989).

McLean et al., "Synthesis and Pharmacological Evaluation of Conjugates of Prednisolone and Non–steroidal Anti–inflammatory Agents", vol. 54, No. 4, *Steroids*, pp. 421–439, (1989).

Makovec et al., "Pharmacokinetics and Metabolism of [14C]–proglumetacin after Oral Administration in the Rat", vol. 37, No. 7, *Arzneim.–Forsch.*, pp. 806–813, (1987).

Boltze et al., "Chemical Structure and Anti–inflammatory Activity in the Group of Substituted Indole–3–acetic Acids", vol. 30, No. 8A, *Arzneim.–Forsch.*, pp. 1314–1325, (1980).

Rojo et al., "Variation in the Immunosuppressive Activity by Structural Modifications of a Series on Non–steroidal Anti–inflammatory Drugs (Indomethacin Esters)", vol. 4, No. 3, *Arch. Farmacol. Toxicol.*, pp. 287–292, (1978).

Barasoain et al., "Indomethacin Esters Acting as Anti–inflammatory and Immunosuppressive Drugs", vol. 16, No. 5, *Int. J. Clin. Pharmacol. Biopharm.*, pp. 235–239, (1978).

Barasoain et al., "Immunosuppressive Effects of some Organic Compounds with Anti–inflammatory Activity", vol. 8, *Chemother., Proc. Int. Cong. Chemother*, pp. 21–26, (1976).

Bonina et al., "In Vitro and In Vivo Evaluation of Polyoxyethylene Indomethacin Esters as Dermal Prodrugs", vol. 34, No. 3 br273, *J. Controlled Release*, pp. 223–232 (1995).

Yamawaki et al., "Piperazinealkanol Ester Derivatives of Indomethacin as Dual Inhibitors of 5–lipoxygenase and Cyclooxygenase", vol. 42, No. 4, *Chem. Pharm. Bull.*, pp. 963–971, (1994).

De Caprariis et al., "Synthesis and Pharmacological Evaluation of Oligoethylene Esters Derivatives as Indomethacin Oral Prodrugs", vol. 83, No. 11, *J. Pharm. Sci.*, pp. 1578–1581, (1994).

Fishernova et al., "Esters of 1–(p–cholorbenzoyl)–5–methoxy–2–methyl–3–indolylacetic Acid", vol. 45, No. 3, *Collect. Czech. Chem. Commun.*, pp. 901–905, (1980).

Flynn et al., "Nonsteroidal Anti–inflammatory Drug Hydroxamic Acids. Dual Inhibitors of Both Cyclooxygenase and 5–lipoxygenase", vol. 33, No. 8, *J. Med. Chem.*, pp. 2070–2072, (1990).

*Physicians' Desk Reference*, 41$^{st}$ Edition, pp. 1304–1310 (1987).

Fisnerova et al., "Esters of 1–(p–chlorobenzoyl)–5–methoxy–2–methyl–3–indolylacetic acid", vol. 95, *Heterocycles*, p. 667, (1981).

"Indole Acid Amides", vol. 62, *Heterocyclic Compounds*, pp. 16197–16198, (1965).

"Pharmacologically Interesting Indomethacin Derivates", vol. 88, *Heterocycles*, p. 373 (1978).

John McMurray, Orgainic Chemistry, Second Edition, pp. 742–745, 1988.*

* cited by examiner

AMIDE DERIVATIVES FOR ANTIANGIOGENIC AND/OR ANTITUMORIGENIC USE

GOVERNMENT INTEREST

This research was funded by a research grant from the National Institutes of Health (Research Grant No. CA47479). Thus, the United States government has certain rights in the invention.

TECHNICAL FIELD

The present invention, in general, relates to conversion of the carboxylic acid moiety of various compounds into amide derivatives of the compounds. More specifically, the present invention relates to secondary amide derivatives of non-steroidal antiinflammatory drugs (NSAIDs), particularly of indomethacin (an NSAID), that exhibit inhibition of cyclooxygenase-2 (COX-2) far exceeding inhibition of cyclooxygenase-1 (COX-1), and also, that still exhibit the analgesic, antiinflammatory, and/or antipyretic effect of the compound, i.e., of the NSAID, and moreover, also exhibit cancer inhibition, i.e., an antiangiogenic and/or antitumorigenic effect, in warm blooded vertebrate animals, including humans.

Table of Abbreviations

| Abbreviations | Definitions |
|---|---|
| NSAID | non-steroidal antiinflammatory drug |
| COOH | carboxylic acid moiety |
| COX | cyclooxygenase |
| $PGH_2$ | prostaglandin $H_2$ |
| $PGD_2$ | prostaglandin $D_2$ |
| PGHS | prostaglandin endoperoxide synthase |
| PER | peroxidase |
| SAR | structure-activity reiationship |
| GI | gastrointestinal |
| $IC_{50}$ | concentration in micromoles of indomethacin (or the indomethacin derivative) at which there is 50% inhibition of COX activity - the lower the $IC_{50}$ is, then the more potent the drug is |
| DMSO | dimethyl sulfoxide |
| $^{14}$C-AA | [1-$^{14}$C]-arachidonic acid |
| HPLC | high performance liquid chromatography |
| TLC | thin layer chromatography |
| mg | milligram |
| kg | kilogram |
| mL | milliliter |
| μM | micromole/liter |
| μL | microliter |
| N | normal (when used in conjunction with acid concentrations) |
| NMR | nuclear magnetic resonance |
| $Et_2O$ | diethyl ether |
| EtOAc | ethyl acetate |
| $Et_3N$ | triethyl amine |
| AcOH | acetic acid |
| $CDCl_3$ | deuterated chloroform |
| rt | room temperature (about 72° F., 22° C.) |
| BOP-Cl | bis(2-oxo-3-oxazolidinyl)phosphonic chloride (sold by Aldrich in Wisconsin), and also see the journal article, Diago-Meseguer, Palomo-Coll, Fernandez-Lizarbe, and Zugaza-Bilbao, "New Reagent for Activating Carboxy Groups; Preparation and Reactions of N,N-Bis[2-oxo-3-oxazolidinyl] phosphorodiamidic Chloride" Synthesis (1980) pp. 547–551 |
| mp | melting point |
| FBS | fetal bovine serum |
| DMEM | Dulbecco's modified essential medium |
| LPS | lipopolysaccharide |
| PBS | phosphate-buffered saline |
| IFN-g | interferon gamma |

BACKGROUND OF THE INVENTION

As discussed in more detail below, the COX enzyme is really two enzymes, COX-1 and COX-2, which serve different physiological and pathophysiological functions. As is well known, at antiinflammatory and/or analgesic doses, indomethacin, aspirin, and other NSAIDs effect great inhibition of COX-1, which protects the lining of the stomach from acid, along with relatively minimal inhibition of COX-2, which provokes inflammation in response to joint injury or a disease like arthritis. Also, certain NSAIDs possess essentially the same inhibitory activity against both COX-1 and COX-2. Thus, zeroing in on inhibition of COX-2 alone has been the goal of drug developers for several years in order to reduce or eliminate the GI irritation caused by COX-1 inhibition.

More specifically, as discussed in Smith, Garavito, and DeWitt, "D. L. Prostaglandin Endoperoxide H Synthases (Cyclooxygenases)-1 and -2", *J. Biol. Chem.*, (1996) Vol. 271, pp. 33157–33160, the pertinent step in prostaglandin and thromboxane biosynthesis involves the conversion of arachidonic acid to $PGH_2$, which is catalyzed by the sequential action of the COX and PER activities of PGHS, as set out in the following reaction scheme:

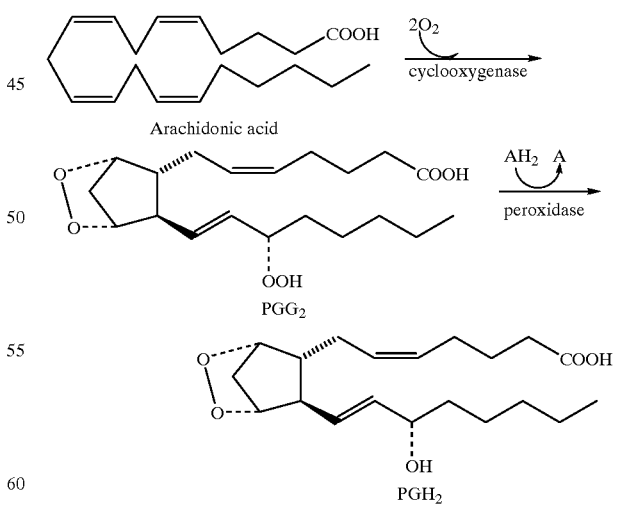

That COX activity originates from two distinct and independently regulated enzymes, termed COX-1 and COX-2, is described in DeWitt and Smith, "Primary Structure of Prostaglandin G/H Synthase from Sheep Vesicular Gland Determined from the Complementary DNA Sequence", *Proc.*

*Natl. Acad. Sci. U.S.A.* (1988) Vol. 85, pp. 1412–1416; Yokoyama and Tanabe, "Cloning of Human Gene Encoding Prostaglandin Endoperoxide Synthase and Primary Structure of the Enzyme", *Biochem. Biophys. Res. Commun.* (1989) Vol. 165, pp. 888–894; and Hla and Neilson, "Human Cyclooxygenase-2-cDNA", *Proc. Natl. Acad. Sci. U.S.A.* (1992) Vol. 89, pp. 7384–7388.

COX-1 is the constitutive isoform and is mainly responsible for the synthesis of cytoprotective prostaglandin in the GI tract and for the synthesis of thromboxane, which triggers platelet aggregation in blood platelets. See, Allison, Howatson, Torrence, Lee, and Russell, "Gastrointestinal Damage Associated with the Use of Nonsteroidal Antiinflammatory Drugs", *N. Engl. J. Med.* (1992) Vol. 327, pp. 749–754.

On the other hand, COX-2 is inducible and short-lived. Its expression is stimulated in response to endotoxins, cytokines, and mitogens. See, Kujubu, Fletcher, Varnum, Lim, and Herschman, "TIS10, A Phorbol Ester Tumor Promoter Inducible mRNA from Swiss 3T3 Cells, Encodes a Novel Prostaglandin Synthase/Cyclooxygenase Homologue", *J. Biol. Chem.* (1991) Vol. 266, pp. 12866–12872; Lee, Soyoola, Chanmugam, Hart, Sun, Zhong, Liou, Simmons, and Hwang, "Selective Expression of Mitogen-Inducible Cyclooxygenase in Macrophages Stimulated with Lipopolysaccharide", *J. Biol. Chem.* (1992) Vol. 267, pp. 25934–25938; and O'Sullivan, Huggins, Jr., and Mccall, "Lipopolysaccharide-lnduced Expression of Prostaglandin H Synthase-2 in Aveolar Macrophages is Inhibited by Dexamethasone by not by Aspirin", *Biochem. Biophys. Res. Commun.* (1993) Vol.191, pp. 1294–1300.

Importantly, COX-2 plays a major role in prostaglandin biosynthesis in inflammatory cells (monocytes/macrophages) and in the central nervous system. See, Masferrer, Zweifel, Manning, Hauser, Leahy, Smith, Isakson, and Seibert, "Selective Inhibition of Inducible Cyclooxygenase-2 in vivo is Antiinflammatory and Nonulcerogenic", *Proc. Natl. Acad. Sci. U.S.A.* (1994) Vol. 91, pp. 3228–3232; Vane, Mitchell, Appleton, Tomlinson, Bishop-Bailey, Croxtall, and Willoughby, "Inducible Isoforms of Cyclooxygenase and Nitric Oxide Synthase in Inflammation", *Proc. Natl. Acad. Sci. U.S.A.* (1994) Vol. 91, pp. 2046–2050; Harada, Hatanaka, Saito, Majima, Ogino, Kawamura, Ohno, Yang, Katori, and Yamamoto, "Detection of Inducible Prostaglandin H Synthase-2 in Cells in the Exudate of Rat Carrageenin-Induced Pleurisy", *Biomed. Res.* (1994) Vol. 15, pp. 127–130; Katori, Harada, Hatanaka, Kawamura, Ohno, Aizawa, and Yamamoto, "Induction of Prostaglandin H Synthase-2 in Rat Carrageenin-Induced Pleurisy and Effect of a Selective COX-2 Inhibitor", *Advances in Prostaglandin, Thromboxane, and Leukotriene Research* (1995) Vol. 23, pp. 345–347; and Kennedy, Chan, Culp, and Cromlish, "Cloning and Expression of Rat Prostaglandin Endoperoxide Synthase (Cyclooxygenase-2) cDNA", *Biochem. Biophys. Res. Commun.* (1994) Vol. 197, pp. 494–500.

Hence, the differential tissue distribution of COX-1 and COX-2 provides a basis for the development of drugs that are selective COX-2 inhibitors (i.e., specificity for inhibition of COX-2 far exceeds inhibition of COX-1) as antiinflammatory, analgesic, and/or antipyretic agents with minimization of or without the GI and hematologic liabilities from COX-1 inhibition that plague most all currently marketed NSAIDs, most of which inhibit both COX-1 and COX-2, with specificity for COX-1 inhibition greatly exceeding that for COX-2 inhibition, although some have essentially similar inhibitory activity against both COX-1 and COX-2. See, for instance, Meade, Smith, and DeWitt, "Differential Inhibition of Prostaglandin Indoperoxide Synthase (Cyclooxygenase) Isozymes by Aspirin and Other Non-Steroidal Antiinflammatory Drugs", *J. Boil. Chem.* , (1993) Vol. 268, pp. 6610–6614.

Detailed SAR studies have been reported for two general structural classes of selective COX-2 inhibitors (specificity for COX-2 inhibition far exceeds COX-1 inhibition) including certain acidic sulfonamides and diarylheterocyclics. The in vivo activities of these selective COX-2 inhibitors validate the concept that selective COX-2 inhibition is antiinflammatory and nonulcerogenic, as discussed in the following journal articles. Gans, Galbraith, Roman, Haber, Kerr, Schmidt, Smith, Hewes, and Ackerman, "Anti-Inflammatory and Safety Profile of DuP 697, a Novel Orally Effective Prostaglandin Synthesis Inhibitor", *J. Pharmacol. Exp. Ther.* (1990) Vol. 254, pp. 180–187; Penning, Talley, Bertenshaw, Carter, Collins, Docter, Graneto, Lee, Malecha, Miyashiro, Rogers, Rogier, Yu, Anderson, Burton, Cogburn, Gregory, Koboldt, Perkins, Seibert, Veenhuizen, Zhang, and Isakson, "Synthesis and Biological Evaluation of the 1,5-Diarylpyrazole Class of Cyclooxygenase-2 Inhibitors: Identification of 4-[5-(4-Methylphenyl)-3 -(trifluoromethyl)-1H-pyrazol-1-yl]benzenesulfonamide (SC-58635, Celecoxib)", *J. Med. Chem.* (1997) Vol. 40, pp.1347–1365; Khanna, Weier, Yu, Xu, Koszyk, Collins, Koboldt, Veenhuizen, Perkins, Casler, Masferrer, Zhang, Gregory, Seibert, and Isakson, "1,2-Diarylimidazoles as Potent Cyclooxygenase-2 Selective, and Orally Active Antiinflammatory Agents", *J. Med. Chem.* (1997) Vol. 40, pp. 1634–1647; Khanna, Weier, Yu, Collins, Miyashiro, Koboldt, Veenhuizen, Curie, Siebert, and Isakson, "1,2-Diarylpyrroles as Potent and Selective Inhibitors of Cyclooxygenase-2", *J. Med. Chem.* (1997) Vol. 40, pp. 1619–1633; Tsuji, Nakamura, Konishi, Tojo, Ochi, Senoh, and Matsuo, "Synthesis and Pharmacological Properties of 1,5-Diarylyrazoles and Related Derivatives", *Chem. Pharm. Bull.* (1997) Vol. 45, pp. 987–995; Riendeau, Percival, Boyce, Brideau, Charleson, Cromlish, Ethier, Evans, Falgueyret, Ford-Hutchinson, Gordon, Greig, Gresser, Guay, Kargman, Léger, Mancini, O'Neill, Quellet, Rodger, Thérien, Wang, Webb, Wong, Xu, Young, Zamboni, Prasit, and Chan, "Biochemical and Pharmacological Profile of a Tetrasubstituted Furanone as a Highly Selective COX-2 Inhibitor", *Br. J. Pharmacol.* (1997) Vol. 121, pp.105–117; Roy, Leblanc, Ball, Brideau, Chan, Chauret, Cromlish, Ethier, Gauthier, Gordon, Greig, Guay, Kargman, Lau, O'Neill, Silva, Thérien, Van Staden, Wong, Xu, and Prasit, "A New Series of Selective COX-2 Inhibitors: 5,6-Diarylthiazolo[3,2-b][1,2,4]-triazoles", *Bioorg. Med. Chem. Lett.* (1997) Vol. 7, pp. 57–62; Thérien, Brideau, Chan, Cromlish, Gauthier, Gordon, Greig, Kargman, Lau, Leblanc, Li, O'Neill, Riendeau, Roy, Wang, Xu, and Prasit, "Synthesis and Biological Evaluation of 5,6-Diarylimidazo[2.1-b]thiazoles as Selective COX-2 Inhibitors", *Bioorg. Med. Chem. Lett.* (1997) Vol. 7, pp.47–52; Li, Norton, Reinhard, Anderson, Gregory, Isakson, Koboldt, Masferrer, Perkins, Seibert, Zhang, Zweifel, and Reitz, "Novel Terphenyls as Selective Cyclooxygenase-2 Inhibitors and Orally Active Anti-Inflammatory Agents", *J. Med. Chem.* (1996) Vol. 39, pp. 1846–1856; Li, Anderson, Burton, Cogburn, Collins, Garland, Gregory, Huang, Isakson, Koboldt, Logusch, Norton, Perkins, Reinhard, Seibert, Veenhuizen, Zhang, and Reitz, "1,2-Diarylcyclopentenes as Selective Cyclooxygenase-2 Inhibitors and Orally Active Anti-Inflammatory Agents", *J. Med. Chem.* (1995) Vol. 38, pp. 4570–4578; Reitz, Li, Norton, Reinhard, Huang, Penick, Collins, and Garland, "Novel 1,2-Diarylcyclopentenes are Selective Potent and Orally Active Cyclooxygenase Inhibitors", *Med. Chem. Res.* (1995) Vol. 5, pp. 351–363; Futaki, Yoshikawa, Hamasaka, Arai, Higuchi, Iizuka, and Otomo, "NS-398, A Novel Nonsteroidal Antiinflammatory Drug with Potent Analgesic and Antipyretic Effects, which Causes Minimal Stomach Lesions", *Gen. Phamacol.* (1993) Vol. 24, pp. 105–110; Wiesenberg-Boetcher, Schweizer, Green, Muller, Maerki, and Pfeilschifter, "The Pharmacological Profile of CGP 28238, A Novel Highly Potent Anti-inflammatory Compound", *Drugs Exptl Clin Res.* (1989) Vol. XV, pp. 501–509; Futaki, Takahashi, Yokoyama, Arai, Higuchi, and Otomo, "NS-398, A New Anti-Inflammatory Agent, Selectively Inhibits Prostaglandin G/H Synthase/Cyclooxygenase (COX-2) Activity in vitro", *Prostaglandins* (1994) Vol. 47, pp. 55–59; Klein, Nusing, Pfeilschifter, and Ullrich, "Selective Inhibition of Cyclooxygenase-2", *Biochem. Pharmacol.* (1994) Vol. 48, pp. 1605–1610; Li, Black, Chan, Ford-Hutchinson, Gauthier, Gordon, Guay, Kargman, Lau, Mancini, Quimet, Roy, Vickers, Wong, Young, Zamboni, and Prasit, "Cyclooxygenase-2 Inhibitors. Synthesis and Pharmacological Activities of 5-Methanesulfonamido-1-indanone Derivatives", *J. Med. Chem.* (1995) Vol. 38, pp. 4897–8905; Prasit, Black, Chan, Ford-Hutchinson, Gauthier, Gordon, Guay, Kargman, Lau, Li, Mancini, Quimet, Roy, Tagari, Vickers, Wong, Young, and Zamboni, "L-745,337: A Selective Cyclooxygenase-2 Inhibitor", *Med. Chem. Res.* (1995) Vol. 5, pp. 364–374; Tanaka, Shimotori, Makino, Aikawa, Inaba, Yoshida, and Takano, "Pharmacological Studies of the New Antiinflammatory Agent 3-Formylamino-7-methylsulfonylamino-6-phenoxy-4H-1-benzopyran-4-one. 1st Communication: Antiinflammatory, Analgesic and Other Related Properties", *Arzniem.-Forsch./Drug Res.* (1992) Vol. 42, pp. 935–944; Nakamura, Tsuji, Konishi, Okumura, and Matsuo, "Studies on Anti-Inflammatory Agents. I. Synthesis and Pharmacological Properties of 2'-(phenylthio) methanesulfonamides and Related Derivatives", *Chem. Pharm. Bull.* (1993) Vol. 41, pp. 894–906; Chan, Boyce, Brideau, Ford-Hutchinson, Gordon, Guay, Hill, Li, Mancini, Penneton, Prasit, Rasori, Riendeau, Roy, Tagari, Vickers, Wong, and Rodger, "Pharmacology of a Selective Cyclooxygenase-2 Inhibitor, L-745,337: A Novel Nonsteroidal Anti-Inflammatory Agent with an Ulcerogenic Sparing Effect in Rat and Nonhuman Primate Stomach", *J. Pharmacol. Exp. Ther.* (1995) Vol. 274, pp. 1531–1537; and Graedon and Graedon, "Pills Promise Relief without Ulcers", The Raleigh, North Carolina News and Observer, p. 8D (Sep. 13, 1998) which addresses, in general terms, the development of celecoxib, meloxicam, and vioxx as selective COX-2 inhibitors.

Representative acidic sulfonamides and diarylheterocyclics that have been reported as selective COX-2 inhibitors in the journal articles mentioned in the above paragraph are:

Acidic Sulfonamides

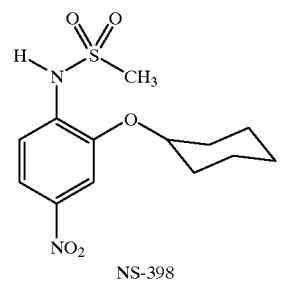

NS-398

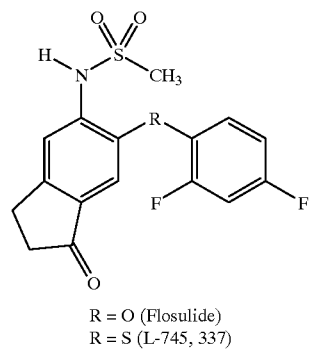

R = O (Flosulide)
R = S (L-745, 337)

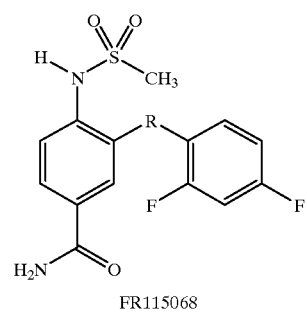

FR115068

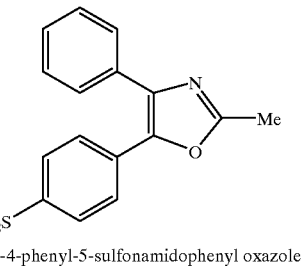

2-methyl-4-phenyl-5-sulfonamidophenyl oxazole

Diarylheterocycles

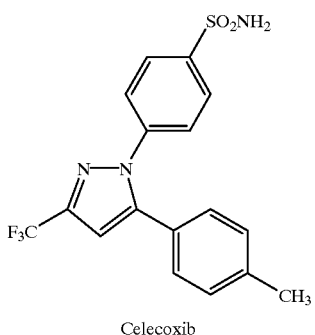

Celecoxib

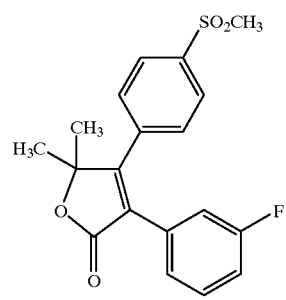

DFU

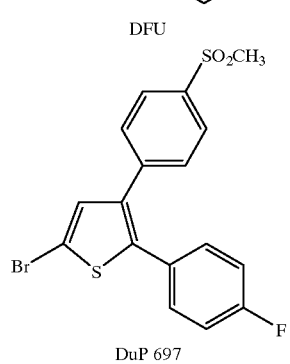

DuP 697

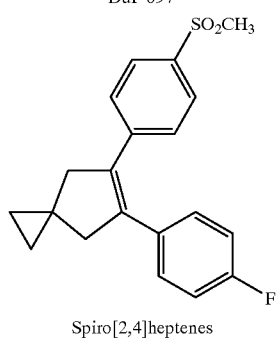

Spiro[2,4]heptenes

Although acidic sulfonamides and diarylheterocyclics have been extensively studied as selective COX-2 inhibitors, there are very few reports on converting NSAIDs that are selective COX-1 inhibitors into selective COX-2 inhibitors. See, Black, Bayly, Belley, Chan, Charleson, Denis, Gauthier, Gordon, Guay, Kargman, Lau, Leblanc, Mancini, Quellet, Percival, Roy, Skorey, Tagari, Vickers, Wong, Xu, and Prasit, "From Indomethacin to a Selective COX-2 Inhibitor: Development of Indolalkanoic Acids as Potent and Selective Cyclooxygenase-2 Inhibitors", *Bioorg. Med. Chem. Lett.* (1996)Vol. 6, pp. 725–730; Luong, Miller, Barnett, Chow, Ramesha, and Browner, "Flexibility of the NSAID Binding Site in the Structure of Human Cyclooxygenase-2", *Nature Structural Biol.* (1996) Vol. 3, pp. 927–933; and Kalgutkar, Crews, Rowlinson, Garner, Seibert, and Marnett, "Aspirin-Like Molecules that Covalently Inactivate Cyclooxygenase-2", Science (1998) Vol. 280, pp. 1268–1270.

Also, interesting is U.S. Pat. No. 5,681,964 (issued in 1997) to Ashton et al., assignors to the University of Kentucky Research Foundation, which shows conversion of indomethacin (an NSAID) into certain ester derivatives with concomitant reduction of GI irritation (see, FIG. 1 of U.S. Pat. No. 5,681,964 for the structure of the ester derivatives). Additionally, U.S. Pat. No. 5,607,966 (Parent)(issued in 1997) and U.S. Pat. No. 5,811,438 (CIP)(issued in 1998), both to Hellberg et al., assignors to Alcon Laboratories, show conversion of various NSAIDs (such as indomethacin) into certain ester derivatives and amide derivatives (which are useful as antioxidants and inhibitors of 5-lipoxygenase) but do not address COX-2 selective inhibition.

Moreover, although U.S. Pat. No. 3,285,908 (issued in 1966) and U.S. Pat. No. 3,336,194 (issued in 1967), both to Shen, assignor to Merck & Co., Inc., describe various secondary and tertiary amide derivatives of indomethacin, the patents fail to address COX inhibition, probably because COX inhibition (both COX-1 and COX-2) was undiscovered in the 1960's, and thus fail to recognize that tertiary amide derivatives do not inhibit either COX-1 or COX-2. (Also, see comparison compounds 9 and 10 in the Examples below.) However, U.S. Pat. No. 5,436,265 (issued in 1995) to Black et al. and U.S. Pat. No. 5,510,368 (issued in 1996) to Lau et al., both patents assigned to Merck Frosst Canada, Inc., describe, respectively, 1-aroyl-3-indolyl alkanoic acids and N-benzyl-3-indoleacetic acids as COX-2 selective inhibitors.

In the present investigation, the possibility has been explored for designing selective COX-2 inhibitors using as templates various compounds, such as NSAIDs, (1) that are selective COX-1 inhibitors or (2) that have essentially the same inhibitory activity for both COX-1 and COX-2. These two kinds of compounds are collectively referred to as compounds that are not selective COX-2 inhibitors.

More particularly, analysis of the human COX-2 crystal structure complexed with zomepirac-derived selective COX-2 inhibitors indicates that the structural basis for selectivity by zomepirac-derived compounds is different from that of diarylheterocyclics. See, Luong et al. mentioned above. Unlike diarylheterocyclics, zomepirac analogs do not utilize the side pocket; instead they breech the constriction at the mouth of the COX active site occupied by Arg106 and Tyr341 and project down the lobby region. The projection into this sterically uncongested region in the COX-2 active site opens the possibility that making a wide range of analogs of COOH-containing NSAIDs, each with a different pendent functional group replacing the OH of the COOH, would accomplish many purposes related to drug discovery or development. For example, certain pendent groups could improve water-solubility, bioavailability, or pharmacokinetics. Another possibility would be to attach a pendent pharmacophore in order to target a completely different protein leading to compounds with dual pharmacological functions.

Abbott Laboratories and Parke-Davis have attempted the pharmacophore approach. See, respectively, Kolasa, Brooks, Rodriques, Summers, Dellaria, Hulkower, Bouska, Bell, and Carter, "Nonsteroidal Anti-Inflammatory Drugs as Scaffolds for the Design of 5-Lipoxygenase Inhibitors", *J. Med. Chem.* (1997) Vol. 40, pp. 819–824; and Flynn, Capiris, Cetenko, Connor, Dyer, Kostlan, Niese, Schrier, and Sircar, "Nonsteroidal Antiinflammatory Drug Hydroxamic Acids. Dual Inhibitors of Both Cyclooxygenase and 5-Lipoxygenase", *J. Med. Chem.* (1990) Vol. 33, pp. 2070–2072. Both Kolasa et al. and Flynn et al. reported that replacement of the carboxylic acid group in NSAIDs with a hydroxamic acid moiety or a hydroxyurea moiety provided dual inhibitors of COX and 5-lipoxygenase. Nevertheless, none of the analogs displayed any significant selective COX-2 inhibition, and furthermore the hydroxamates underwent facile hydrolysis.

However, nothing in the above-discussed literature suggests that converting a COOH-containing drug, such as a COOH-containing NSAID, that is not selective for COX-2 inhibition into a derivative that is selective for COX-2 inhibition would also result in that derivative being a cancer inhibitor. Nevertheless, it is interesting to note that sulindac sulfide (an NSAID which contains a COOH moiety as well as a methyl sulfide moiety) is a 40-fold more potent inhibitor against COX-1 than COX-2, yet also exhibits inhibition of tumors. On the other hand, a derivative, namely sulindac sulfone (which contains a COOH moiety as well as a methyl sulfone moiety) does not inhibit either COX-1 or COX-2, but still exhibits inhibition of tumors.

Thus, it would be desirable to find certain COOH-containing drugs, such as COOH-containing NSAIDs, which are not selective COX-2 inhibitors (either display an inhibition for COX-1 far exceeding inhibition of COX-2 or display essentially the same inhibition for COX-1 and COX-2) that would, when converted into certain derivatives, become selective COX-2 inhibitors (display an inhibition for COX-2 far exceeding inhibition for COX-1), as well as retain the analgesic, antiinflammatory, and/orantipyretic effect of the drug, and yet exhibit other effects not exhibited by the drug prior to derivatization, such as cancer inhibition.

SUMMARY AND OBJECTS OF THE INVENTION

Surprisingly with the present invention, it has been found that derivatization of the carboxylic acid moiety of certain compounds, such as certain NSAIDs, that are not selective COX-2 inhibitors, such as indomethacin, into secondary amide analogs creates isozyme specificity for COX-2. Moreover, the resultant secondary amide derivative is not only a selective COX-2 inhibitor, but also is a cancer inhibitor, i.e., exhibits antiangiogenic and/or antitumorigenic activity, and preferably, also retains the analgesic, antiinflammatory, and/or antipyretic of the compound.

Therefore, the present invention provides a method for cancer treatment in a warm blooded vertebrate animal. The method comprises administering to the animal a treatment effective amount sufficient to inhibit cancer of a carboxylic acid secondary amide derivative of a compound. The derivative is selective for inhibition of cyclooxygenase-2. The compound (a) is a cyclooxygenase inhibitor but is not selective for inhibition of cyclooxygenase-2 and (b) contains a carboxylic acid moiety or a pharmaceutically acceptable salt thereof. Preferably, the compound is a non-steroidal antiinflammatory drug, or a pharmaceutically acceptable salt thereof.

Hence, it is an object of the invention to provide a cancer treatment that minimizes or obviates GI irritation.

Moreover, it is an advantage of the present invention that the cancer treatment is also analgesic, antiinflammatory, and/or antipyretic, absent the concomitant administration of an analgesic, antiinflammatory, and/or antipyretic drug, such as an NSAID or a pharmaceutically acceptable salt thereof.

Some of the objects of the invention having been stated above, other objects will become evident as the description proceeds, when taken in connection with the Laboratory Examples as described below.

DETAILED DESCRIPTION OF THE INVENTION

The present invention involves a method for treating cancer in an animal that is a warm-blooded vertebrate. Therefore, the invention concerns mammals and birds.

Contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans.

Thus, contemplated is the treatment of livestock, including, but not limited to, domesticated swine (pigs and hogs), ruminants, horses, poultry, and the like.

More particularly, a treatment effective amount of a secondary amide derivative of a carboxylic acid-containing compound is administered to the warm-blooded vertebrate animal. Thus, the invention comprises administration of the secondary amide derivative in concentrations calculated to provide the animal being treated with the appropriate milieu to provide prevention, control, or cessation of cancer. Moreover, in the preferred embodiment, the secondary amide derivative possesses an analgesic, antiinflammatory, and/or antipyretic property as possessed by the carboxylic acid-containing compound prior to derivatization, and thus, the cancer treatment provides an analgesic, antiinflammatory, and/or antipyretic effect in the animal and is free of concomitant administration of another drug for providing such effect.

By carboxylic-acid containing compound or COOH-containing compound as used herein in connection with the present invention, it is intended to include pharmaceutically acceptable acid salts of the compound. Thus, for instance, the COOH moiety includes COOM, where M is Na and the like.

The derivatives useful in the method of the present invention are secondary amide derivatives of drugs having a carboxylic acid moiety or a pharmaceutically acceptable salt thereof, for instance, secondary amide derivatives of non-steroidal anti-inflammatory drugs having a carboxylic acid moiety or a pharmaceutically acceptable salt thereof. A number of chemical classes of non-steroidal anti-inflammatory drugs have been identified, as described in *CRC Handbook of Eicosanoids: Prostaglandins, and Related Lipids, Volume II, Drugs Acting Via the Eicosanoids*, pages 59–133, CRC Press, Boca Raton, Fla. (1989).

The NSAID may be selected, therefore, from a variety of chemical classes including, but not limited to, fenamic acids, such as flufenamic acid, niflumic acid, and mefenamic acid; indoles, such as indomethacin, sulindac, and tolmetin; phenylalkanoic acids, such as suprofen, ketorolac, flurbiprofen, and ibuprofen; and phenylacetic acids, such as diclofenac. Further examples of NSAIDs are listed below:

| | | |
|---|---|---|
| aceloferac | etodolic acid | loxoprofen |
| alcofenac | fenbufen | meclofenamate |
| amfenac | fenclofenac | naproxen |
| benoxaprofen | fenclorac | orpanoxin |
| bromfenac | fenoprofen | pirprofen |
| carprofen | fleclozic acid | pranoprofen |
| clidanac | indoprofen | tolfenamic acid |
| diflunisal | isofezolac | zaltoprofen |
| efenamic acid | ketoprofen | zomopirac |

More specifically, preferred secondary amide derivatives useful in the present invention include, but are not limited to, secondary amide derivatives of the following COOH-containing NSAIDs: 6-methoxy-α-methyl-2-naphthylacetic acid (and its Na acid salt form known as naproxen), meclofenamic acid, and diclofenac, with secondary amide derivatives of indomethacin being preferred, and that indomethacin derivative described below as compound 11 being especially preferred. Also, the secondary amide derivatives of indomethacin, where the Cl at the 4-position of the benzoyl moiety is replaced with Br or F, should work in the present invention.

Even more preferred are the secondary amide derivatives of indomethacin including, but are not limited to, indomethacin-N-methyl amide, indomethacin-N-ethan-2-ol amide, indomethacin-N-octyl amide, indomethacin-N-nonyl amide, indomethacin-N-(2-methylbenzyl) amide, indomethacin-N-(4-methylbenzyl) amide, indomethacin-N-((R)-,4-dimethylbenzyl) amide, indomethacin-N-((S)-,4-dimethylbenzyl) amide, indomethacin-N-(2-phenethyl) amide, indomethacin-N-(4-fluorophenyl) amide, indomethacin-N-(4-chlorophenyl) amide, indomethacin-N-(4-acetamidophenyl) amide, indomethacin-N-(4-methylmercapto)phenyl amide, indomethacin-N-(3-methylmercaptophenyl) amide, indomethacin-N-(4-methoxyphenyl) amide, indomethacin-N-(3-ethoxyphenyl) amide, indomethacin-N-(3,4,5-trimethoxyphenyl) amide, indomethacin-N-(3-pyridyl) amide, indomethacin-N-5-((2-chloro)pyridyl) amide, indomethacin-N-5-((1-ethyl) pyrazolo) amide, indomethacin-N-(3-chloropropyl) amide, indomethacin-N-methoxycarbonylmethyl amide, indomethacin-N-2-(2-L-methoxycarbonylethyl) amide, indomethacin-N-2-(2-D-methoxycarbonylethyl) amide, indomethacin-N-(4-methoxycarbonylbenzyl) amide, indomethacin-N-(4-methoxycarbonylmethylphenyl) amide, indomethacin-N-(2-pyrazinyl) amide, indomethacin-N-2-(4-methylthiazolyl) amide, indomethacin-N-(4-biphenyl) amide, and combinations thereof.

The secondary amide derivative may be administered to the animal as a suppository or as a supplement to fluids that are administered internally or parenterally, for instance nutriment fluids such as intervenous sucrose solutions. Furthermore, intraoral (such as buccal or sublingual) administration or transdermal (such as with a skin patch) administration to the animal is also contemplated. A good discussion of intraoral administration can be seen in U.S. Pat. No. 4,229,447 issued Oct. 21,1980 to Porter and U.S. Pat. No. 5,504,086 issued Apr. 2,1996 to Ellinwood and Gupta. A good discussion of transdermal administration can be seen in U.S. Pat. No. 5,016,652 issued May 21, 1991 to Rose and Jarvik.

Additionally, administration to the animal may be by various oral methods, for instance as a tablet, capsule, or powder (crystalline form) that is swallowed. Also, oral administration may include that the secondary amide derivative is admixed in a carrier fluid appropriate therefore so that it is administered as a liquid (solution or suspension) that is drunk. When the secondary amide derivative is admixed in a carrier fluid, appropriate fluids include, but are not limited to, water, rehydration solutions (i.e., water with electrolytes such as potassium citrate and sodium chloride, for instance the solution available under the trade name RESOL® from Wyeth Laboratories), nutritional fluids (i.e., milk, fruit juice), and combinations thereof. Thus, the oral administration may be as a component of the diet, such as human food, animal feed, and combinations thereof.

In addition to oral administration such as by way of the mouth, contemplated also is administration of a solution or suspension to the esophagus, stomach, and/or duodenum, such as by gavage, i.e., by way of a feeding tube. Gavage type of administration is useful for when the cancer has progressed and the animal can no longer swallow food, medicine, et cetera, by mouth.

Hence, it is also contemplated that additional ingredients, such as various excipients, carriers, surfactants, nutriments, and the like, as well as various medicaments other than a secondary amide derivative, or combinations thereof, may be present together with the secondary amide derivative, whatever the form that the derivative is in. Medicaments other than a secondary amide derivative may include, but are not limited to, osmolytic polyols and osmolytic amino acids (i.e., myo-inositol, sorbitol, glycine, alanine, glutamine, glutamate, aspartate, proline, and taurine), cardiotonics (i.e., glycocyamine), analgesics, antibiotics, electrolytes (i.e., organic or mineral electrolytes such as salts), and combinations thereof.

A suitable dosing amount of secondary amide derivative for administration to the animal should range from about 0.5 mg to about 7.0 mg per kg of body weight of the animal per day, more preferably from about 1.5 mg to about 6.0 mg per kg of body weight of the animal per day, and even more preferably from about 2.0 mg to about 5.0 mg per kg of body weight of the animal per day. Administration may be one or more times per day to achieve the total desired daily dose. Of course, the amount can vary depending on the severity of the cancer and/or the age of the animal.

The present invention should be useful in the treatment of cancer in animals, wherein the cancer is caused by pathogens (i.e., parasites, bacteria, protozoa, and viruses, including toxic agents in food), nutritional factors (i.e., excess mineral salts, excess protein, allergic agents in food, undigestible food components, or poor quality ingredients in food), environmental factors that act as stressors or pollutants (i.e., heat, chilling, shipment of animals, or toxins such as from air and/or water pollution), and/or physiological disorders such as those of the digestive tract, pulmonary/circulatory system, liver, kidneys, colon, and/or pancreas.

The present invention indicates that COOH-containing drugs that are not COX-2 selective inhibitors, such as the NSAID known as indomethacin, when converted into secondary amides, results in isozyme specificity for COX-2 and thus presents an efficient strategy for the generation of potent and selective COX-2 inhibitors. The below-discussed extensive SAR study conducted with indomethacin suggests that a variety of secondary amide substituents are tolerated for replacing the OH in the COOH moiety of indomethacin, and these resultant derivatives are as potent and selective as COX-2 inhibitors as are the diarylheterocyclics discussed above. Thus, this strategy has great potential in the development of nonulcerogenic antiinflammatory agents. Moreover, as illustrated in the Examples below, the secondary amide derivatives of the invention also exhibit an anticancer effect.

LABORATORY EXAMPLES

The following is noted in connection with the materials and procedures below.

The amides that were made and their selective COX-2 inhibition properties are listed in the Table below. A total of 31 analogs (31 amide derivatives) of indomethacin were prepared. Various nitrogen-containing substituents (i.e., amines) that replaced the OH of the COOH, in order to create an amide, included aminoalkyl, aminoaryl, aminoarylalkyl, aminoethers, or aminopyridinyl moieties as part of the nitrogen-containing substituent. The most potent amide analogs in the indomethacin derivative series displayed $IC_{50}$ values for inhibition of purified human COX-2 in the low nanomolar range with COX-2 selectivity ratios ranging from >1000 to 4000.

Well established methodology was utilized in the synthesis of amide derivatives of indomethacin by treatment of the indomethacin with an appropriate amine (designated as R) utilizing BOP-Cl as the carboxylic acid activator to replace the OH of the COOH with R and create an amide. If R was a primary amine, the resultant derivative was a secondary amide, and if R was a secondary amine, the resultant derivative was a tertiary amide.

More specifically, a reaction mixture containing indomethacin (300 mg, 0.84 mmol) and BOP-Cl(218 mg, 0.84 mmol) in 5 mL of anhydrous $CH_2Cl_2$ was treated with $Et_3N$ (167 mg, 0.84 mmol) and allowed to stir at rt for 10 minutes. The mixture was then treated with the appropriate amine (0.94 mmol) designated as R and stirred overnight at rt. Following dilution with $CH_2Cl_2$ (30 mL), the resultant solution was washed with water (2×25 mL), 3 N NaOH (2×25 mL), water (2×30 mL), dried (in the presence of $MgSO_4$), filtered, and the solvent concentrated in vacuo. The crude amide was purified by chromatography on silica gel or recrystallization in the appropriate solvent. The reaction scheme was as follows:

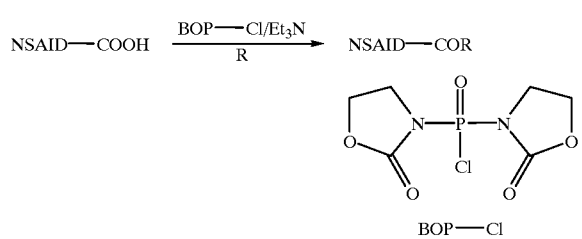

$IC_{50}$ values for the inhibition of purified human COX-2 or ovine COX-1 by test compounds were determined by the TLC assay discussed below. Ovine COX-1 was used because it is very easy to isolate and to purify the enzyme from sheep seminal vesicles, whereas human COX-1 is normally 15 obtained by over expression in an insect cell system and is very difficult to handle and especially to purify. COX-1 from sheep is >90% similar to COX-1 from humans. Finally, inhibition of COX-1 from these two sources by NSAIDs has been reported in the published literature and the $IC_{50}$ values are similar, suggesting no dramatic active site differences. COX-1 was purified from ram seminal vesicles obtained from Oxford Biomedical Research, Inc. (Oxford, Mich.). The specific activity of the protein was 20 ($\mu MO_2$/minute)/mg, and the percentage of holoprotein was 13.5%. Samples of human COX-2 (1.62 $\mu g/\mu l$) were obtained by expression of insect cell cloned human COX-2 carried on baculovirus vectors, followed by purification.

The enzymes obtained after purification were apo (i.e., they lacked the hemprosthetic group). They were reconstituted with hematin purchased from Sigma Chemical Co. (St. Louis, Mo.) in the assays to render them to their natural states which is holo (i.e., natural COX-1 and natural COX-2 contain the hemprosthetic group) so that the inhibition by test compounds had physiological relevance.

HoloCOX-2 (66 nM) or holoCOX-1 (44 nM) in 100 mM Tris-HCl, pH 8.0 containing 500 $\mu M$ phenol was treated with several concentrations of indomethacin or an amide derivative of indomethacin at 25° C. for 20 minutes. Since the recombinant COX-2 had a lower specific activity than the ovine COX-1, the protein concentrations were adjusted such that the percentages of total products obtained following catalysis of arachidonic acid (purchased from Nu Chek Prep, Elysian, Minn.) by the two isoforms were comparable.

More specifically, time- and concentration-dependent inhibition of cyclooxygenase activity for ovine COX-1 (44 nM) and human COX-2 (66 nM) using the TLC assay was determined as follows. Reaction mixtures of 200 μL contained hematin-reconstituted protein in 100 mM Tris-HCl, pH 8.0, 500 μM phenol, and [1-$^{14}$C]-arachidonic acid (50 μM, ~55–57 mCi/mmol). For the time-dependent inhibition assay, hematin-reconstituted COX-1 (44 nM) or COX-2 (66 nM) was preincubated at rt for 20 minutes with varying inhibitor concentrations in DMSO followed by the addition of [1-$^{14}$C]-arachidonic acid (50 μM) for 30 seconds at 37° C. [1-$^{14}$C]-arachidonic acid (~55–57 mCi/mmol) was purchased from New England Nuclear, Dupont, or American Radiolabeled Chemicals (St. Louis, Mo.).

Reactions were terminated by solvent extraction in Et$_2$O/ CH$_3$OH/1 M citrate, pH 4.0 (30:4:1). The phases were separated by centrifugation at 2000 g-force for 2 minutes and the organic phase was spotted on a TLC plate (obtained from J. T. Baker, Phillipsburg, N.J.). The plate was developed in EtOAc/CH$_2$Cl$_2$/glacial AcOH (75:25:1) at 4° C. Radiolabeled prostanoid products were quantitatively determined with a radioactivity scanner (obtained from Bioscan, Inc., Washington, D.C.). The percentage of total products observed at different inhibitor concentrations was divided by the percentage of products observed for protein samples preincubated for the same time with DMSO.

Control experiments in the absence of indomethacin indicated ~25–30% conversion of fatty acid substrate to products, which was sufficient for assessing the inhibitory properties of all test compounds. Under these conditions, indomethacin displayed selective time- and concentration-dependent inhibition of COX-1 (i.e., IC$_{50}$ (COX-1)~0.050 μM; IC$_{50}$ (COX-2)~0.75 μM), whereas the secondary amide derivatives displayed selective COX-2 inhibition and the tertiary amide derivatives did not inhibit either COX-1 or COX-2 (i.e., measurement of COX-2 was stopped at an extremely high IC$_{50}$ and still >80% COX-2 activity remained). Also, the following is noted for NS-398 and 2-methyl-4-phenyl-5-sulfoamidophenyl oxazole, which are two of the above-mentioned acidic sulfonamides: namely, NS-398: IC$_{50}$ (COX-2)~0.12 μM; IC$_{50}$ (COX-1)>66 μM; and 2-methyl-4-phenyl-5-sulfoamidophenyl oxazole: IC$_{50}$ (COX-2)~0.06 μM; IC$_{50}$ (COX-1)>66 μM.

For certain comparison tests, inhibition of COX-2 activity in activated murine RAW264.7 cells was determined as follows. Low passage number murine RAW264.7 cells were grown in DMEM containing 10% heat-inactivated FBS. Cells (6.2×10$^6$ cells/T25 flask) were activated with 500 ng/mL LPS and 10 units/mL IFN-g in serum-free DMEM for 7 hours. Vehicle (DMSO) or inhibitor in DMSO (0 to 1 μM) was added for 30 minutes at 37° C. Inhibition of exogenous arachidonic acid metabolism or inhibition of PGD$_2$ synthesis was determined by incubating the respective cells with 20 μM $^{14}$C-AA for 15 minutes at 25° C. Aliquots (200 μL) were removed into termination solution and total products were quantitatively determined by the TLC assay as described earlier.

Melting points were determined using a Gallenkamp melting point apparatus and were uncorrected. Chemical yields were unoptimized specific examples of one preparation. NSAIDs (i.e., indomethacin) were purchased from Sigma (St. Louis, Mo.). All other chemicals were purchased from Aldrich (Milwaukee, Wis.). Methylene chloride was purchased as anhydrous from Aldrich and was used as received. All other solvents were HPLC grade. Analytical TLC (Analtech uniplates™) was used to follow the course of reactions. Silica gel (Fisher, 60–100 mesh) was used for column chromatography. $^1$H NMR and $^{13}$C NMR spectra in CDCl$_3$ were recorded on a Bruker WP-360 spectrometer or an AM-400 spectrometer. Chemical shifts were expressed in parts per million (ppm) relative to tetramethylsilane as an internal standard. Spin multiplicities were reported as s (singlet), d (doublet), dd (doublet of doublets), t (triplet), q (quartet), and m (multiplet). Coupling constants (J) were reported in hertz (Hz).

Example I

The following carboxylic acid amide derivatives of indomethacin, designated as compounds 1 through 31, were made. (Note: compounds 1, 2, and 9 through 13 are also disclosed in the above-discussed U.S. Pat. Nos. 3,285,908 and 3,336,194, both to Shen, assignor to Merck & Co., Inc.)

Indomethacin-N-methyl amide (compound 1) was obtained upon chromatography on silica gel (EtOAc:hexanes; 10:90 then 50:50) as a bright yellow solid (271 mg, 79%). mp=187–189° C.; $^1$H NMR (CDCl$_3$) δ 7.64–7.67 (dd, 2 H, J=6.6 Hz and 1.9 Hz, ArH), 7.47–7.50 (dd, 2 H, J=6.7 Hz and 1.9 Hz, ArH), 6.88–6.89 (dd, 1 H, J=9.1 Hz and 2.5 Hz, ArH), 6.84–6.87 (d, 1 H, J=9.0 Hz, ArH), 6.68–6.72 (dd, 1 H, J=9.1 Hz and 2.5 Hz, ArH), 5.22 (bs, 1 H, NH), 3.83 (s, 3 H, CH$_3$), 3.65 (s, 2 H, CH$_2$), 2.75–2.76 (d, 3 H, J=4.8 Hz, CH$_3$), 2.39 (s, 3 H, CH$_3$).

Indomethacin-N-ethan-2-ol amide (compound 2) was obtained upon chromatography on silica gel (EtOAc) as a pale yellow solid (143 mg, 39%). mp=162–164° C.; $^1$H NMR (CDCl$_3$) δ 7.66–7.68 (dd, 2 H, J=6.7 Hz and 1.7 Hz, ArH), 7.47–7.50 (dd, 2 H, J=6.9 Hz and 1.9 Hz, ArH), 6.85–6.89 (d and s, 2 H, J=9.2 Hz, ArH), 6.68–6.72 (dd, 1 H, J=9.0 Hz and 2.5 Hz, ArH), 6.03 (bs, 1 H, NH), 3.82 (s, 3 H, CH$_3$), 3.67 (bs, 4 H, 2CH$_2$), 3.35–3.40 (q, 2 H, J=4.8 Hz, CH$_2$), 2.44 (bs, 1 H, OH), 2.39 (s, 3 H, CH$_3$).

Indomethacin-N-octyl amide (compound 3) was obtained upon chromatography on silica gel (EtOAc:hexanes; 30:70) as a yellow solid (164 mg, 42%). mp=109–111° C.; $^1$H NMR (CDCl$_3$) δ 7.62–7.65 (d, 2H, J=8.2 Hz, ArH), 7.46–7.49 (d, 2H, J=8.2 Hz, ArH), 6.85–6.89 (m, 2H, ArH), 6.68–6.71 (d, 1H, J=8.9 Hz, ArH), 5.67 (s, 1H, NH), 3.82 (s, 3H, CH$_3$), 3.64 (s, 2H, CH$_2$), 3.16–3.22 (m, 2H, CH$_2$), 2.38 (s, 3H, CH$_3$), 1.39 (m, 2H, CH$_2$), 1.19 (m, 10 H, 5CH$_2$), 0.83–0.88 (t, J=6.2 Hz, CH$_3$).

Indomethacin-N-nonyl amide (compound 4) was obtained upon chromatography on silica gel (EtOAc:hexanes; 30:70) as a yellow solid (191 mg, 47%).%). mp=128–130° C.; $_1$H NMR (CDCl$_3$) δ 7.64–7.67 (d, 2H, J=8.4 Hz, ArH), 7.47–7.50 (d, 2H, J=8.4 Hz, ArH), 6.89 (s, 1H, ArH), 6.85–6.88 (d, J=8.9 Hz, ArH), 6.68–6.72 (dd, 1H, J=9.0 Hz and 2.4 Hz, ArH), 5.60–5.63 (bt, J=5.3 Hz, NH), 3.82 (s, 3H, CH$_3$),3.64 (s, 2H, CH$_2$),3.16–3.22 (m, 2H, CH$_2$), 2.38 (s, 3H, CH$_3$), 1.36–1.41 (m, 2H, CH$_2$),1.19–1.28 (m, 12H, 6CH$_2$), 0.84–0.89 (t, J=6.5 Hz, CH$_3$).

Indomethacin-N-(2-methylbenzyl) amide (compound 5) was obtained upon chromatography on silica gel (EtOAc:hexanes; 50:50) as a yellow solid (218 mg, 56%). mp=177–179° C.; $^1$H NMR (CDCl$_3$) δ 7.60–7.61 (d, 2H, J=8.1 Hz, ArH), 7.44–7.46 (d, 2H, J=8.1 Hz, ArH), 7.06–7.15 (m, 4H, ArH), 6.83–6.89 (m, 2H, ArH), 6.67–6.70 (d, 1H, J=8.1 Hz, ArH), 5.84 (s, 1H, NH), 4.40–4.41 (d, 2H, J=5.3 Hz, CH$_2$), 3.79 (s, 3H, CH$_3$), 3.70 (s, 2H, CH$_2$), 2.37 (s, 3H, CH$_3$), 2.19 (s, 3H, CH$_3$).

Indomethacin-N-(4-methylbenzyl) amide (compound 6) was obtained upon recrystallization from methanol as a yellow solid (142 mg, 37%). mp=191–192° C.; $^1$H NMR (CDCl$_3$) δ 7.63–7.60 (d, 2H, J=8.5 Hz, ArH), 7.46–7.44 (d, 2H, J=8.4 Hz, ArH), 7.08–7.01 (m, 4H, ArH), 6.88 (s, 1H, ArH), 6.87–6.85 (d, 1H, J=6.3 Hz, ArH), 6.71–6.67 (dd, 1H, J=9.0 Hz and 2.4 Hz, ArH), 5.89 (bt, 1H, NH), 4.38–4.36 (d, 2H, J=5.9 Hz, CH$_2$), 3.78 (s, 3H, CH$_3$), 3.69 (s, 2H, CH$_2$), 2.35 (s, 3H, CH$_3$), 2.30 (s, 3H, CH$_3$).

Indomethacin-N-((R)-4-dimethylbenzyl) amide (compound 7) was obtained upon recrystallization from methanol to yield a pale yellow solid (124 mg, 31%). mp=201–202° C.; $^1$H NMR (CDCl$_3$) δ 7.62–7.64 (d, 2H, J=8.4 Hz, ArH), 7.45–7.48 (d, 2H, J=8.6 Hz, ArH), 7.01–7.08 (m, 4H, ArH), 6.87–6.90 (d, 1H, J=9.0 Hz, ArH), 6.83–6.84 (d, 1H, J=2.3 Hz, ArH), 6.68–6.72 (dd, 1H, J=9.0 Hz and 2.4 Hz, ArH), 5.76–5.78 (bd, 1H, J=8.0 Hz, NH), 5.09–5.14 (m, 1H, CH), 3.76 (s, 3H, CH$_3$), 3.63–3.64 (d, 2H, J=2.8 Hz, CH$_2$), 2.34 (s, 3H, CH$_3$), 2.30 (s,3H, CH$_3$), 1.35–1.38 (d, 3H, J=6.8 Hz, CH$_3$).

Indomethacin-N-((S)-4-dimethylbenzyl) amide (compound 8) was obtained upon recrystallization from methanol as a pale yellow solid (163 mg, 41%). mp=200–201° C.; $^1$H NMR (CDCl$_3$) δ 7.53–7.55 (d, 2H, J=8.3 Hz, ArH), 7.37–7.40 (d, 2H, J=8.4 Hz, ArH), 6.94–7.01 (m, 4H, ArH), 6.76–6.82 (m, 2H, ArH), 6.61–6.64 (dd, 1H, J=9.0 Hz and 2.5 Hz, ArH) 5.77–5.79 (bd, 1 H, J=7.8 Hz, NH), 5.02–5.07 (m, 1H, CH), 3.69 (s, 3H, CH$_3$), 3.58–3.59 (d, 2H, J=2.9 Hz CH$_2$), 2.27 (s, 3H, CH$_3$), 2.23 (s, 3H, CH$_3$), 1.28–1.30 (d, 3H, J=6.9 Hz CH$_3$).
Comparison.

Indomethacin-N-methylphenethyl amide (compound 9) was obtained upon chromatography on silica gel (EtOAc:hexanes; 50:50) as a yellow solid (288 mg, 72%). mp=61–63° C.; $^1$H NMR (CDCl$_3$) δ 7.64–7.67 (d, 2H, J=8.4 Hz, ArH), 7.45–7.48 (d, 2H, J=8.5 Hz, ArH), 7.02 (d, 1H, J=2.4 Hz, ArH), 6.81–6.84 (d, 1H, J=9.0 Hz, ArH), 6.63–6.66 (dd, 1H, J=9.0 Hz and 2.5 Hz, ArH), 3.82 (s, 3H, CH$_3$), 3.71 (s, 2H, CH$_2$), 3.57–3.60 (t, 2H, J=5.4 Hz, CH$_2$), 3.43–3.46 (t, 2H, J=5.3 Hz, CH$_2$), 2.38 (s, 3H, CH$_3$), 1.59–1.61 (m, 2H, CH$_2$), 1.52–1.53 (m, 2H, CH$_2$), 1.42–1.43 (m, 2H, CH$_2$).
Comparison.

Indomethacin-N-piperidinyl amide (compound 10) was obtained upon chromatography on silica gel (EtOAc:hexanes; 40:60) as a pale yellow solid (146 mg, 41%). mp=161–163° C.; $^1$H NMR (CDClmethoxycarbonylmethyl$_3$) δ 7.64–7.67 (d, 2H, J=8.4 Hz, ArH), 7.45–7.48 (d, 2H, J=8.5 Hz, ArH), 7.02 (d, 1H, J=2.4 Hz, ArH), 6.81–6.84 (d, 1H, J=9.0 Hz, ArH), 6.63–6.66 (dd, 1H, J=9.0 Hz and 2.5 Hz, ArH), 3.82 (s, 3H, CH$_3$), 3.71 (s, 2H, CH$_2$),3.57–3.60 (t, 2H, J=5.4 Hz, CH$_2$), 3.43–3.46 (t, 2H, J=5.3 Hz, CH$_2$), 2.38 (s, 3H, CH$_3$), 1.59–1.61 (m, 2H, CH$_2$), 1.52–1.53 (m, 2H, CH$_2$), 1.42–1.43 (m, 2H, CH$_2$).

Indomethacin-N-(2-phenethyl) amide (compound 11) was obtained upon chromatography on silica gel (EtOAc:hexanes; 30:70) as a bright yellow solid (169 mg, 44%). mp=148–150° C.; $_1$H NMR (CDCl$_3$) δ 7.58–7.60 (d, J=8.4 Hz, ArH), 7.46–7.48 (d, 2H, J=8.5 Hz, ArH), 7.12–7.14 (m, 3H, ArH), 6.85–6.95 (m, 4H, ArH), 6.69–6.73 (dd, 1H, J=8.9 Hz and 2.4 Hz, ArH), 5.61 (s, 1H, NH), 3.81 (s, 3H, CH$_3$), 3.59 (s, 2H, CH$_2$), 3.43–3.49 (m, 2H, CH$_2$), 2.68–2.72 (t, 2H, J=6.7 Hz, CH$_2$), 2.04 (s, 3H, CH$_3$).

Indomethacin-N-(4-fluorophenyl) amide (compound 12) was obtained upon chromatography on silica gel (EtOAc:hexanes; 5:95 to 20:80) as an orange solid (217 mg, 57%). mp=200–202° C.; $_1$H NMR (CDCl$_3$) δ 7.65–7.67 (d, 2H, J=8.3 Hz, ArH), 7.47–7.50 (d, 2H, J=8.3 Hz, ArH), 7.32–7.35 (m, 3H, ArH), 6.94–6.99 (m, 3H, ArH, NH), 6.85–6.88 (d, 1H, J=9.0 Hz, ArH), 6.70–6.73 (dd, 1H, J=9.0 Hz and 2.0 Hz, ArH), 3.81 (s, 3H, CH$_3$), 3.79 (s, 2H, CH$_2$), 2.45 (s, 3H, CH$_3$).

Indomethacin-N-(4-chlorophenyl) amide (compound 13) was obtained upon recrystallization from methanol as a pale yellow solid (234 mg, 56%). mp=209–210° C.; $^1$H NMR (CDCl$_3$) δ 7.58–7.61 (d, 2H, J=8.2 Hz, ArH), 7.40–7.42 (d, 2H, J=8.2 Hz, ArH), 7.13–7.27 (m, 5H, ArH), 6.84 (s, 1H, NH), 6.77–6.80 (d, 1H, J=9.0 Hz, ArH), 6.62–6.65 (d, 1H, J=9.0 Hz, ArH), 3.72 (s, 2H, CH$_2$), 3.72 (s, 3H, CH$_3$), 2.37 (s, 3H, CH$_3$).

Indomethacin-N-(4-acetamidophenyl) amide (compound 14) was obtained upon recrystallization from methanol as a pale yellow solid (221 mg, 54%). mp=256–257° C.; $^1$H NMR (DMSO-d$_6$) δ 10.14 (s, 1H, NH), 9.86 (s, 1H, NH), 7.62–7.70 (m, 4H, ArH), 7.48 (s, 4H, ArH), 7.18 (d, 1H, J=2.3 Hz, ArH), 6.90–6.93 (d,1H, J=9.0 Hz, ArH), 6.68–6.72 (dd, 1H, J=9.1 Hz and 2.5 Hz, ArH), 3.73 (s, 3H, CH$_3$), 3.71 (s, 2H, CH$_2$), 2.27 (s, 3H, CH$_3$), 1.99 (s, 3H, CH$_3$).

Indomethacin-N-(4-methylmercapto)phenyl amide (compound 15) was obtained upon chromatography on silica gel (EtOAc:hexanes; 50:50) as a bright yellow solid (162 mg, 40%). mp=195–196° C.; $^1$H NMR (CDCl$_3$) δ 7.67–7.70 (d, 2H, J=8.4 Hz, ArH), 7.48–7.50 (d, 2 H, J=8.4 Hz, ArH), 7.30–7.33 (d, 2 H, J=8.6 Hz, ArH), 7.17–7.22 (m, 3 H, 2 ArH and NH), 6.92–6.93 (d, 1 H, J=2.3 Hz, ArH), 6.85–6.88 (d, 1 H, J=9.0 Hz, ArH), 6.69–6.73 (dd, 1 H, J=9.0 Hz and 2.4 Hz, ArH), 3.80 (s, 3 H, CH$_3$), 3.79 (s, 2 H, CH$_2$), 2.45 (s, 3 H, C$_3$), 2.44 (s, 3 H, CH$_3$).

Indomethacin-N-(3-methylmercaptophenyl) amide (compound 16) was obtained upon chromatography on silica gel (EtOAc:hexanes; 15:85) as a yellow solid (218 mg, 54%). mp=129–131° C.; $^1$H NMR (CDCl$_3$) δ 7.62–7.64 (d, 2H, J=8.2 Hz, ArH), 7.45–7.48 (d, 2H, J=8.4 Hz, ArH), 7.39 (s, 1H, NH), 7.09–7.18 (m, 2H, ArH), 6.94–6.96 (m, 3H, ArH), 6.86–6.89 (d, 1H, J=9.0 Hz), 6.69–6.72 (d,1 H, J=8.9 Hz, ArH), 3.80 (s, 3H, CH$_3$), 3.78 (s, 2H, CH$_2$), 2.42 (s, 3H, CH$_3$).

Indomethacin-N-(4-methoxyphenyl) amide (compound 17) was obtained upon chromatography on silica gel (EtOAc:hexanes; 10:90 to 25:75) as an orange solid (239 mg, 61%). mp=201–202° C.; $^1$H NMR (CDCl$_3$) δ 7.67–7.70 (dd, 2H, J=6.8 Hz and 1.8 Hz, ArH), 7.48–7.51 (d, 2H, J=7.1 Hz, ArH), 7.28–7.29 (d, 1H, J=2.0 Hz, ArH), 7.20 (s, 1H, NH), 6.94–6.95 (d, 1H, J=2.4 Hz, ArH), 6.86–6.89 (d, 1H, J=9.0 Hz, ArH), 6.78–6.84 (m, 2H, ArH), 6.69–6.73 (dd, 1H, J=9.0 Hz and 2.4 Hz, ArH), 3.81 (s, 3H, CH$_3$, 3.79 (s, 2H, CH$_2$), 3.76 (s, 3H, CH$_3$), 2.45 (s, 3H, CH$_3$).

Indomethacin-N-(3-ethoxyphenyl) amide (compound 18) was obtained upon recrystallization from methanol as a bright yellow solid (297 mg, 74%). mp=152–154° C.; $^1$H NMR (CDCl$_3$) δ 7.68–7.70 (d, 2H, J=8.4 Hz, ArH), 7.48–7.51 (d, 2H, J=8.4 Hz, ArH), 7.24 (s, 1H, NH), 7.13–7.18 (m, 2H, ArH), 6.94–6.82 (m, 3H, ArH), 6.70–6.73 (dd, 1H, J=9.0 Hz and 2.4 Hz), 6.61–6.65 (dd, 1H, J=8.2 Hz and 1.7 Hz, ArH), 3.96–4.03 (q, 2H, J=7.0 Hz, CH$_2$), 3.81 (s, 3H, CH$_3$), 3.80 (s, 2H, CH$_2$), 2.45 (s, 3H, CH$_3$), 1.36–1.40 (t, 3H, J=7.0 Hz, CH$_3$).

Indomethacin-N-(3,4,5-trimethoxyphenyl) amide (compound 19) was obtained upon chromatography on silica gel (EtOAc:hexanes; 10:90 to 30:70) as a light orange solid (191 mg, 44%). mp=239–241° C.; $^1$H NMR (CDCl$_3$) δ 7.67–7.69 (d, 2H, J=8.5 Hz, ArH), 7.48–7.51 (d, 2H, J=8.5 Hz, ArH), 7.20 (s, 1H, NH), 6.94 (d, 1H, J=8.9 Hz, ArH), 6.70–6.74 (m, 3H, ArH), 3.78–3.81 (m, 14H, 3CH$_3$ & CH$_2$), 2.45 (s, 3H, CH$_3$).

Indomethacin-N-(3-pyridyl) amide (compound 20) was obtained upon chromatography on silica gel (EtOAc:hexanes; 50:50 to 75:25) as a yellow solid (190 mg, 52%). mp=204–205° C.; $^1$H NMR (CDCl$_3$) δ 8.39–8.40 (d, 1H, J=2.1 Hz, ArH), 8.32–8.34 (d, 1H, J=4.4 Hz, ArH), 8.04–8.08 (m, 1H, ArH), 7.66–7.70 (m, 2H, ArH), 7.48–7.52 (m, 2H, ArH), 7.38 (s, 1H, NH), 7.22–7.25 (m, 1H, ArH), 6.93–6.94 (d, 1H, J=2.4 Hz, ArH), 6.85–6.88 (d, 1H, J=9.1 Hz, ArH), 6.70–6.74 (dd, 1H, J=9.1 Hz and 2.5 Hz, ArH), 3.84 (s, 2H, CH$_2$), 3.81 (s, 3H, CH$_3$), 2.47 (s, 3H, CH$_3$).

Indomethacin-N-5-((2-chloro)pyridyl) amide (compound 21) was obtained upon chromatography on silica gel (EtOAc:hexanes; 5:95 to 50:50) as a pale yellow solid (221 mg, 56%). mp=196–198° C.; $^1$H NMR (CDCl$_3$) δ 8.19–8.20 (d, 1H, J=2.8 Hz, ArH), 8.03–8.06 (dd, 1H, J=8.7 Hz and 2.9 Hz, ArH), 7.59–7.63 (m, 2H, ArH), 7.46–7.51 (m, 3H, ArH), 7.24 (s, 1H, NH), 6.92–6.93 (d, 1H, J=2.4 Hz, ArH), 6.84–6.87 (d, 1H, J=9.0 Hz, ArH), 6.70–6.74 (dd, 1H, J=9.1 Hz and 2.5 Hz, ArH), 3.84 (s, 2H, CH$_2$), 3.82 (s, 3H, CH$_3$), 2.46 (s 3H, CH$_3$).

Indomethacin-N-5-((1-ethyl)pyrazolo) amide (compound 22) was obtained upon recrystallization from methanol as a pale yellow solid (153 mg, 40%). mp=193–194° C.; $^1$H NMR (CDCl$_3$) δ 7.99 (bs, 1H, NH), 7.66–7.68 (d, 2H, J=8.2 Hz, ArH), 7.47–7.50 (m, 3H, ArH), 7.00 (s, 1H, ArH), 6.83–6.86 (d, 1H, J=9.0 Hz, ArH), 6.69–6.72 (d, 1H, J=8.9 Hz, ArH), 6.35 (s, 1H, ArH), 4.01–4.04 (bd, 2H, J=6.8 Hz, CH$_2$), 3.90 (s, 2H, CH$_2$), 3.82 (s, 3H, CH$_3$), 2.47 (s, 3H, CH$_3$), 1.24–1.29 (t, 3H, J=7.1 Hz, CH$_3$).

Indomethacin-N-(3-chloropropyl) amide (compound 23) was obtained upon chromatography on silica gel (EtOAc:hexanes; 30:70) as a off-white solid (153 mg, 40%). $^1$H NMR (DMSO-d$_6$) δ 8.11 (bs, 1H, NH), 7.62–7.69 (m, 4H, ArH), 7.09 (s, 1 H. ArH), 6.92–6.95 (d, 1 H, J=8.9 Hz, ArH), 6.68–6.71 (d, 1 H, J=8.8 Hz, ArH), 3.80 (s, 3H, CH$_3$),3.58–3.67 (t, 2 H, J=6.3 Hz, CH$_2$), 3.52 (s, 2H, CH$_2$),3.15–3.17 (m, 2 H, CH$_2$),2.20 (s, 3H, CH$_3$), 1.81–1.85 (t, 2 H, J=6.5 Hz, CH$_2$).

Indomethacin-N-methoxycarbonylmethyl amide (compound 24) was obtained upon chromatography on silica gel (EtOAc:hexanes; 30:70) as a yellow solid (265 mg, 76%). $^1$H NMR (CDCl$_3$) δ 7.66–7.68 (dd, 2 H, J =6.7 Hz and 1.7 Hz, ArH), 7.47–7.50 (dd, 2 H, J=6.9 Hz and 1.9 Hz, ArH), 6.92–6.95 (m, 2 H, ArH), 6.70–6.73 (m, 1 H, ArH), 6.03 (bs, 1 H, NH), 3.98–4.00 (d, 2 H, J=5.5 Hz, CH$_2$),3.84 (s, 3 H, CH$_3$),3.71 (s, 3 H, CH$_3$), 3.69 (s, 2 H, CH$_2$), 2.38 (s, 3 H, CH$_3$).

Indomethacin-N-2-(2-L-methoxycarbonylethyl) amide (compound25) was obtained upon chromatography on silica gel (EtOAc:hexanes; 30:70 and then 50:50) as a yellow solid (300 mg, 84%). $^1$H NMR (CDCl$_3$) δ 7.67–7.70 (dd, 2 H, J=8.5 Hz and 1.85 Hz, ArH), 7.47–7.50 (dd, 2 H, J=8.4 Hz and 1.9 Hz, ArH), 6.91–6.96 (m, 2 H, ArH), 6.69–6.73 (m, 1 H, ArH), 6.16–6.18 (d, 1 H, J=7.4 Hz, NH), 4.57–4.62 (m, 1 H, CH), 3.83 (s, 3 H, CH$_3$),3.70 (s, 3 H, CH$_3$), 3.65 (s, 2 H, CH$_2$), 2.37 (s, 3 H, CH$_3$), 1.32–1.34 (d, 3 H, J=7.2 Hz, CH$_3$).

Indomethacin-N-2-(2-D-methoxycarbonylethyl) amide (compound26) was obtained upon chromatography on silica gel (EtOAc:hexanes; 40:60) as a yellow solid (803 mg, 67%). $^1$H NMR (CDCl$_3$) δ 7.67–7.70 (dd, 2 H, J=8.5 Hz and 1.85 Hz, ArH), 7.47–7.50 (dd, 2 H, J=8.4 Hz and 1.9 Hz, ArH), 6.91–6.96 (m, 2 H, ArH), 6.69–6.73 (dd, 1 H, ArH), 6.16–6.18 (d, 1 H, J=7.4 Hz, NH), 4.57–4.62 (m, 1 H, CH), 3.83 (s, 3 H, CH$_3$), 3.70 (s, 3 H, CH$_3$), 3.65 (s, 2 H, CH$_2$), 2.36 (s, 3 H, CH$_3$), 1.32–1.34 (d, 3 H, J=7.2 Hz, CH$_3$).

Indomethacin-N-(4-methoxycarbonylbenzyl) amide (compound 27) was obtained upon chromatography on silica gel (EtOAc:hexanes; 40:60) as a yellow solid (198 mg, 47%). $^1$H NMR (CDCl$_3$) δ 7.91–7.94 (d, 2 H, J=6.8 Hz, ArH), 7.61–7.65 (d, 2H, J=8.7 Hz, ArH), 7.45–7.48 (d, 2H, J=9.0 Hz, ArH), 7.19–7.21 (d, 2H, J =8.3 Hz, ArH), 6.83–6.88 (m, 2H, ArH), 6.68–6.72 (dd, 1 H, J=9.0 Hz and 2.4 Hz, ArH), 5.97–5.99 (bt, 1H, J=5.9 Hz, NH), 4.45–4.47 (d, 2H, J=6.1 Hz, CH$_2$), 3.90 (s, 3H, CH$_3$), 3.83 (s, 3H, CH$_3$), 3.72 (s, 2H, 2.38 (s, 3H, CH$_3$).

Indomethacin-N-(4-methoxycarbonylmethylphenyl) amide (compound 28) was obtained upon chromatography on silica gel (EtOAc:hexanes; 20:80) as an yellow solid (100 mg, 23%). $^1$H NMR (CDCl$_3$) δ 7.67–7.70 (d, 2H, J=8.5 Hz, ArH), 7.48–7.51 (d, 2H, J=8.5 Hz, ArH), 7.33–7.36 (d, 2H, J =8.4 Hz, ArH), 7.18–7.23 (d and bs, 3 H, ArH and NH), 6.92–6.93 (d, 1 H, J=2.3 Hz, ArH), 6.85–6.88 (d, 1H, J=9.0 Hz, ArH), 6.70–6.73 (dd, 1H, J=9.0 Hz and 2.0 Hz, ArH), 3.81 (s, 5H, CH$_2$ and CH$_3$), 3.67 (s, 3H, CH$_3$), 3.56 (s, 3H, CH$_2$), 2.45 (s, 3H, CH$_3$).

Indomethacin-N-(2-pyrazinyl) amide (compound 29) was obtained upon chromatography on silica gel (EtOAc:hexanes; 30:70 to 50:50) as a bright yellow solid (251 mg, 69%). $^1$H NMR (CDCl$_3$) δ 9.58 (d, 1 H, J=1.4 Hz, ArH), 8.33–8.34 (d, 1 H, J=2.5 Hz, ArH), 8.16–8.17 (m, 1 H, ArH), 7.86 (bs, 1 H, NH), 7.69–7.71 (d, 2H, J=8.5 Hz, ArH), 7.49–7.51 (d, 2H, J=8.5 Hz, ArH), 6.92–6.93 (d, 1 H, J=2.4 Hz, ArH), 6.84–6.87 (d, 1 H, J=8.9 Hz, ArH), 6.70–6.72 (dd, 1 H, J=9.0 Hz and 2.5 Hz, ArH), 3.86 (s, 2H, CH$_2$), 3.81 (s, 3H, CH$_3$), 2.47 (s, 3H, CH$_3$).

Indomethacin-N-2-(4-methylthiazolyl) amide (compound 30) was obtained upon chromatography on silica gel (EtOAc:hexanes; 30:70 and then 70:30) to afford the pure product as a pale yellow solid which was recrystallized from ethyl ether (241 mg, 63%). $^1$H NMR (CDCl$_3$) δ 8.68 (bs, 1 H, NH), 7.70–7.74 (d, 2 H, J =9.0Hz, ArH), 7.48–7.52 (d, 2 H, J=9.0 Hz, ArH), 6.79–6.85 (m, 2 H, ArH), 6.67–6.71 (dd, 1 H, J=9.0 Hz and 2.4 Hz, ArH), 6.52 (s, 1 H, Thiazole-H), 3.88 (s, 2 H, CH$_2$), 3.79 (s, 3 H, CH$_3$), 2.45 (s, 3 H, CH$_3$), 2.27 (s 3 H, CH$_3$).

Indomethacin-N-(4-biphenyl) amide (compound 31) was obtained upon chromatography on silica gel (EtOAc:hexanes; 30:70) to afford the pure product as a pale yellow solid (421 mg, 59%). $^1$H NMR (CDCl$_3$) δ 7.68–7.71 (d, 2 H, J=8.4 Hz, ArH), 7.32–7.55 (m, 11 H, ArH), 6.95–6.96 (d, 1 H, J=2.0 Hz, ArH), 6.86–6.89 (d, 1 H, J=9.0 Hz, ArH), 6.73–6.74 (dd, 1 H, J=1.7 Hz, ArH), 3.83 (s, 2 H, CH$_2$), 3.81 (s, 3 H, CH$_3$), 2.47 (s, 3 H, CH$_3$).

The structures and IC$_{50}$ values for indomethacin and Compounds 1 through 31 are set out in the Table below.

TABLE

Selective COX-2 Inhibition by Amide Derivatives of Indomethacin

| Compound | R | IC$_{50}$ (μM)[a] COX-2 | COX-1 | Selectivity[b] |
|---|---|---|---|---|
| Indomethacin | OH | 0.75 | 0.05 | 0.066 |
| 1 | NHCH$_3$ | 0.70 | >66[2] | >94 |
| 2 | HN-CH$_2$CH$_2$-OH | 0.25 | >66 | 287 |
| 3 | HN-(CH$_2$)$_7$CH$_3$ | 0.0375 | 66 | 1760 |
| 4 | HN-(CH$_2$)$_9$CH$_3$ | 0.04 | 16.5 | 412.5 |
| 5 | HN-CH$_2$-(2-methylphenyl) | 0.15 | >66[c] | >440 |
| 6 | HN-CH$_2$-(4-methylphenyl) | 0.06 | 8.0 | 133 |
| 7 | HN-CH(CH$_3$)-(4-methylphenyl) (R) | 0.0625 | 4.0 | 64 |
| 8 | HN-CH(CH$_3$)-(4-methylphenyl) (S) | 0.20 | 4.0 | 20 |

TABLE-continued
Selective COX-2 Inhibition by Amide Derivatives of Indomethacin
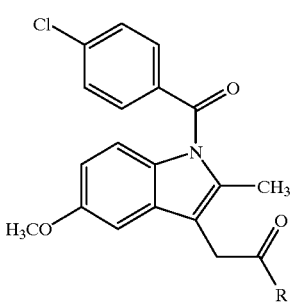
| Compound | R | IC$_{50}$ ($\mu$M)[a] COX-2 | COX-1 | Selectivity[b] |
|---|---|---|---|---|
| 9 (Comparison) | 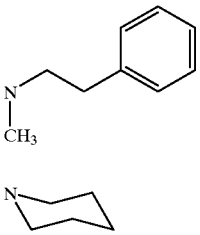 | >33[c] | >66 | — |
| 10 (Comparison) | 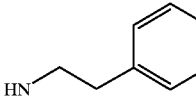 | >33[c] | >66 | — |
| 11 | 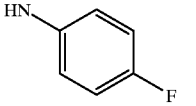 | 0.06 | >66 | >1100 |
| 12 | 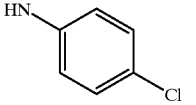 | 0.06 | >66[c] | >1100 |
| 13 | 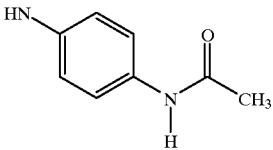 | 0.062 | >66[c] | >1064 |
| 14 | 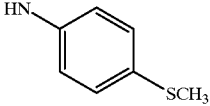 | 0.12 | >66[c] | >550 |
| 15 | 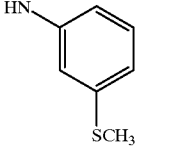 | 0.12 | >66[c] | >550 |
| 16 |  | 0.22 | >66[c] | >300 |

TABLE-continued
Selective COX-2 Inhibition by Amide Derivatives of Indomethacin
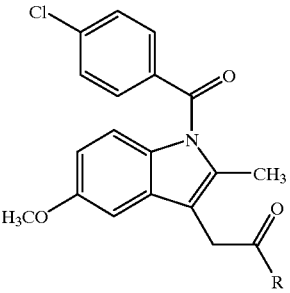
| Compound | R | IC$_{50}$ ($\mu$M)[a] COX-2 | COX-1 | Selectivity[b] |
|---|---|---|---|---|
| 17 | 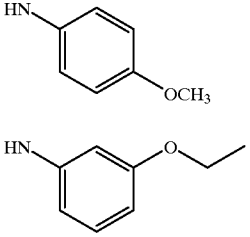 | 0.056 | >66[c] | >1178 |
| 18 | 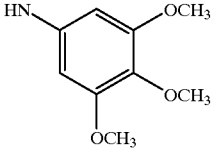 | 0.65 | 52.5 | 81 |
| 19 | 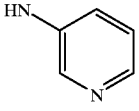 | >1.0 | >66 | >66 |
| 20 | 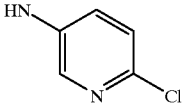 | 0.052 | >66 | >1269 |
| 21 | 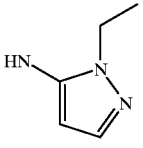 | 0.047 | >66[c] | >1404 |
| 22 | 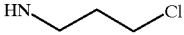 | 0.70 | >66[c] | >94 |
| 23 | HN⌒⌒Cl | 0.050 | 45 | 900 |
| 24 | 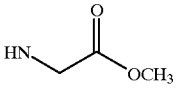 | 4.0 | >66 | >16.5 |
| 25 | 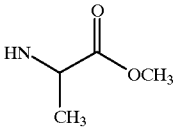 | 0.4 | >66 | >165 |

TABLE-continued

Selective COX-2 Inhibition by Amide Derivatives of Indomethacin

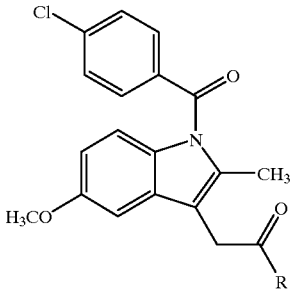

| Compound | R | IC$_{50}$ ($\mu$M)$^a$ | | Selectivity$^b$ |
| --- | --- | --- | --- | --- |
| | | COX-2 | COX-1 | |
| 26 | 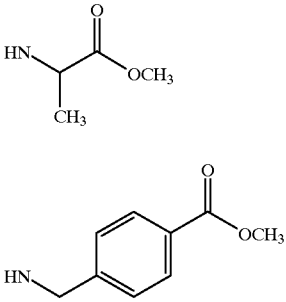 | 0.19 | >66 | >347 |
| 27 | 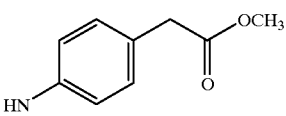 | 0.080 | >66 | >825 |
| 28 | 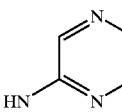 | 0.058 | >66 | >1138 |
| 29 | 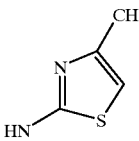 | 4.0 | >66 | >16.5 |
| 30 | 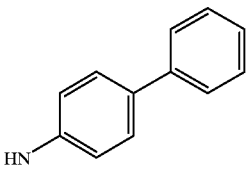 | 4.0 | >66 | >16.5 |
| 31 |  | 0.5 | >66 | >132 |

$^a$IC$_{50}$ values were determined by incubating several concn of inhibitor in DMSO with human COX-2 (66 nM) or ovine COX-1 (44 nM) for 20 min followed by treatment with 1-$^{14}$C-AA (50 $\mu$M) at 37° C. for 30 sec. Assays were run in duplicate.
$^b$Ratio of IC$_{50}$ (COX-1):IC$_{50}$ (COX-2).
$^c$>80% remaining COX-1 activity at this concn Discussion of Secondary Amide Derivatives of Indomethacin Carboxylic Acid Aliphatic Secondary Amides Derivatives of Indomethacin.

The N-methyl amide derivative (compound 1) displayed selective COX-2 inhibition (IC$_{50}$ (COX-2)~0.70 $\mu$M; IC$_{50}$ (COX-1)>66 $\mu$M). Increments in COX-2 inhibitory potency and selectivity was observed with the higher octyl homolog (compound 3); however, further increase in chain length to the nonyl derivative (compound 4) led to some loss of COX-2 selectivity (compound 3: IC$_{50}$ (COX-2)~37.5 nM; IC$_{50}$ (COX-1) 66 μM; compound 4: IC$_{50}$ (COX-2)~40 nM; IC$_{50}$ (COX-1)~16.5 μM).

Carboxylic Acid Aromatic Secondary Amides Derivatives of Indomethacin.

Incorporation of methylene spacer units (compound 11) between the amide nitrogen and the phenyl ring also generated potent and selective COX-2 inhibitors.

For instance, the 4-methylbenzyl amide derivative (compound 6) was 133-fold selective for COX-2, whereas the corresponding 2-methylbenzyl isomer (compound 5) was >440 times more selective as a COX-2 inhibitor. Furthermore, the R-methyl-(4-methylbenzyl) enantiomer (compound 7) was a better inhibitor of COX-2 than the corresponding S-methyl enantiomer (compound 8).

Additionally, the aromatic amides containing the 4-fluoro (compound 12), 4-methylmercapto (compound 15), or the 3-pyridyl substituent (compound 20), displayed potent and selective COX-2 inhibition, as noted below.

Compound 12

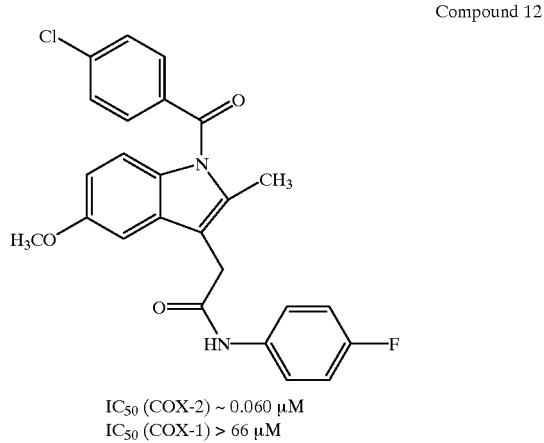

IC$_{50}$ (COX-2) ~ 0.060 μM
IC$_{50}$ (COX-1) > 66 μM

Compound 15

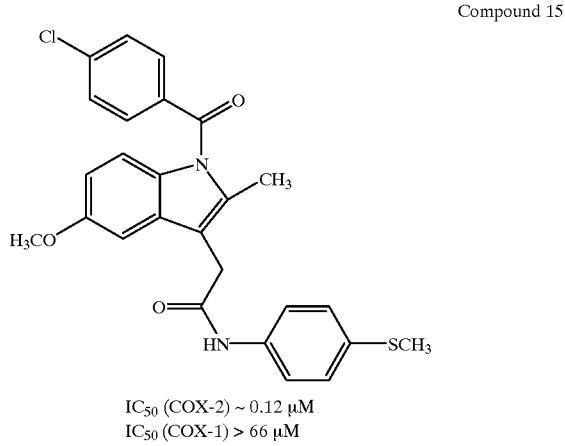

IC$_{50}$ (COX-2) ~ 0.12 μM
IC$_{50}$ (COX-1) > 66 μM

-continued

Compound 20

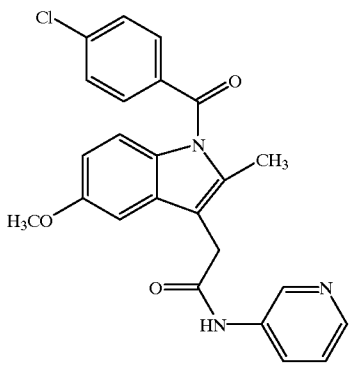

IC$_{50}$ (COX-2) ~ 0.052 μM
IC$_{50}$ (COX-1) > 66 μM

Tertiary Amides (Comparison compounds 9 and 10).

Another interesting aspect in the SAR studies with the indomethacin amides was that N,N-methyl-2-phenethyl (compound 9) and the piperidinyl (compound 10) amide derivatives, both of which are tertiary amides, were inactive against COX-2. In other words, only the secondary amides were selective COX-2 inhibitors, whereas the tertiary amides were devoid of any inhibitory effect towards either isozyme i.e., measurement of COX-2 inhibition for the tertiary amides was stopped at an extremely high IC value (see the value of 33 for both compounds 9 and 10) and still >80% COX-1 activity remained.

Example II

Comparison with Sulfonamides of Another Study.

A similar SAR study was previously reported in the above-noted journal article by Li et al. for acidic sulfonamides. (See, the structures drawn above for compounds L-745,337 and NS-398.) Specifically, Li et al. found that replacement of the N-H proton in the NHSO$_2$CH$_3$ moiety of L-745,337 or NS-398 with a methyl group led to complete loss of inhibitory potency towards either the COX-1 or COX-2 isozyme.

This behaviour may be explained from the recently solved crystal structure of murine COX-2 complexed with NS-398. See, Kurumbail et al., Abstract 197, Eicosanoids and Other Bioactive Lipids in Cancer, Inflammation and Related Diseases, *Fifth International Conference*, La Jolla, Calif. (17–20 September 1997). Unlike the diarylheterocyclics, NS-398 does not utilize the side pocket even though it contains a sulfonamide group. Instead the sulfonamide binds to Arg106 in a fashion similar to the carboxylic acid-containing NSAIDs.

Although the carboxylic acid secondary amide derivatives of indomethacin in the present invention do not contain any electron-withdrawing substituents, the above-discussed SAR observations on the lack of inhibition by the carboxylic acid tertiary amide derivatives suggest that the -CONH-$R_1$ group probably binds to a group on the enzyme (see below). This can be seen from contrasting the data immediately below for the inventive secondary amide derivative (compound 11) with the comparison tertiary amide derivatives (compounds 9 and 10) and the comparison derivative of prior art compound NS-398 in which the N-H proton in the $NHSO_2CH_3$ moiety was replaced with methyl.

Compound 11

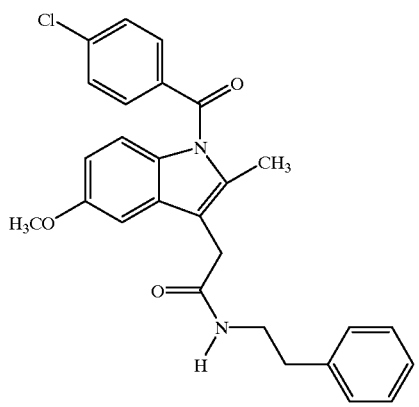

$IC_{50}$ (COX-2) ~ 0.060 μM
$IC_{50}$ (COX-1) > 66 μM

Compound 9

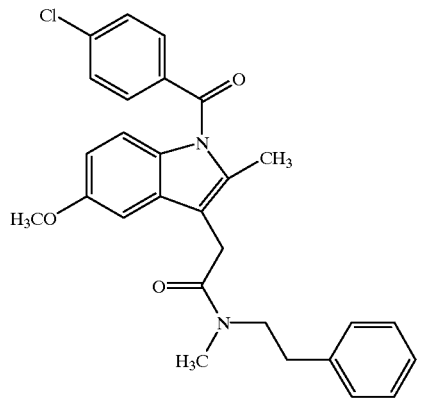

$IC_{50}$ (COX-2) ~ 0.12 μM
$IC_{50}$ (COX-1) > 66 μM

Compound 10

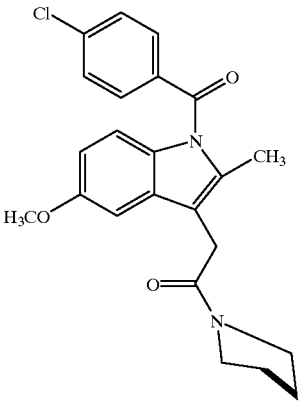

$IC_{50}$ (COX-2) ~ 33 μM
$IC_{50}$ (COX-1) > 66 μM

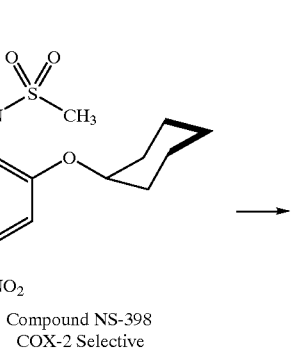

Compound NS-398
COX-2 Selective

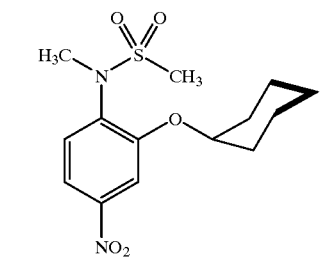

Inactive against either isoform COX-1 or COX-2 when proton replaced with methyl

Example III
Additional Inhibitory Activity Testing with Mouse COX.

Compound 11. The structural basis for COX-2 selectivity by compound 11 also was probed by site directed mutagenesis. More particularly, the inhibitory potency of indomethacin as compared to that of indomethacin-N-phenethyl amide (compound 11) was evaluated against site directed murine COX-2 mutants (Arg106Gln and Tyr341Ala) which represent key residues involved in the binding of the carboxylic acid-containing NSAIDs. Arg106 is the only positively charged residue in the fatty acid binding site and is important for binding the carboxylic acid moiety of an NSAID with Tyr341Ala, which is juxtaposed to Arg106 at the constriction site and is responsible for the selective binding of the S-enantiomers but not the R-enantiomers in the 2-phenylpropionate class of NSAIDs including flurbiprofen. In addition to these mutants, also analyzed was the inhibition profile of the Val509IleArg499HisVal420Ile mutant (also known as the VRV mutant) which incorporates the major amino acid changes between COX-2 and COX-1 in the side pocket region and is responsible for binding the diarylheterocycles. The results were that indomethacin displayed a slightly better potency against wild-type mouse COX-2 than compound 11 (indomethacin: $IC_{50}$ (mouse COX-2)~25 nM; compound 11: $IC_{50}$ (mouse COX-2)~35 nM). Furthermore, the Tyr341Ala and the triple mutant VRV was resistant to inhibition by each of indomethacin and compound 11, whereas the Arg 106Gln mutant was resistant to inhibition by indomethacin but was effectively inhibited by compound 11 ($IC_{50}$~25 nM).

Compound 17. Inhibition of COX-2 activity in intact mouse cells by Compound 17 was assayed in murine RAW264.7 macrophages in which COX-2 activity was induced by pathologic stimuli. The macrophages were treated with LPS (500 ng/mL) and interferon-g (10 U/mL) for 7.5 hours to induce COX-2 and then treated with several concentrations of the 4-methoxyphenyl amide derivative of indomethacin (compound 17) for 30 minutes at 37° C. The $IC_{50}$ value for $PGD_2$ by compound 17 was 62.5 nM. Under these conditions, indomethacin was a better inhibitor of COX-2 activity in intact mouse cells ($IC_{50}$~10 nM) than compound 17.

Indeed, comparison of the potency of indomethacin as a inhibitor of purified mouse COX-2 versus purified human COX-2 revealed that indomethacin displayed greater inhibition of the mouse enzyme than of the human isoform ($IC_{50}$ (mouse COX-2)~350 nM; $IC_{50}$ (human COX-2)~1 $\mu$M). On the other hand, an indomethacin-amide derivative (compound 11) was a better inhibitor of human COX-2 than of murine COX-2 (compound 11: $IC_{50}$ (mouse COX-2)~120 nM; $IC_{50}$ (human COX-2)~75 nM).

These results also strengthen another researcher's previous observations which suggest that COX enzymes from the rat are pharmacologically different from those from humans, as reported in Ramesha, "Human and Rat Cyclooxygenases are Pharmacologically Distinct", *Adv. Exp. Med. Biol.* (1997) Vol. 407, pp. 67–71.

Example IV
Testing for Reduction in Inflammation.

Compound 14 was tested in a standard in vivo assay of inflammation—the rat foot pad edema model. This assay is widely used in the pharmaceutical industry to evaluate antiinflammatory compounds. Rats were injected with carrageenan, which triggers a rapid edema (swelling) within 3 hours that can be quantitatively measured by volume displacement. A single dose of compound 14 (2 mg/kg) given orally 1 hour after carrageenan injection caused a dramatic decrease in swelling.

In these experiments, the carrageenan that was injected was in 0.1 mL of aqueous saline so that 0.1 mL volume increase was due to the injection alone. Taking this into consideration, approximately an 80–85% reduction in inflammation following treatment with compound 14 was found. For comparison, indomethacin was also tested in this assay at a dose of 2 mg/kg orally, and comparable reduction in inflammation was found.

More specifically, male Sprague-Dawley rats (150 g) received a subplantar injection of carrageenan (0.1 mL of a 1% suspension of carrageenan in sterile aqueous saline) into the right hind footpad while mildly anesthetized with methoxyflurane. At 1 hour post-injection, the rats were gavaged with 0.5 mL corn oil containing either 90 $\mu$L DMSO or 90 $\mu$L compound 14 for the doses specified below. The ipsilateral footpad volume (mL) was measured with a water displacement plethysmometer at time=3 hours post-injection and compared to the time=0 pre-injection paw volume for edema calculations.

For each dose, 6 rats were injected, and the results are summarized below.

| | Compound 14 | |
|---|---|---|
| Concentration (mg/mL) | 3 hour edema (mL) | standard deviation |
| 0 | 0.87 | 0.1 |
| 0.2 | 0.55 | 0.04 |
| 0.5 | 0.47 | 0.07 |
| 1.0 | 0.39 | 0.03 |
| 2.0 | 0.38 | 0.07 |

Example V
Testing for Tumor Inhibition.

The ability of compound 11 to inhibit the growth of a human colon cancer cell line in nude mice (human tumor xenograft assay) was determined. Following subcutaneous inoculation of the mice with the human tumor cells, the animals were injected intraperitoneally 3 times a week with vehicle alone or vehicle containing 5 mg/kg of compound 11.

More specifically, male athymic Nude-nu (nu/nu) mice (25 g, 6–8 weeks old, Harlan Sprague-Dawley) were injected intraperitoneally with 100 $\mu$L vehicle (5% ethanol, 5% Tween 80 in sterile aqueous PBS) or 100 $\mu$L compound 11 in vehicle immediately prior to subcutaneous implantation of $5 \times 10^6$ HCA-7 (human colon adenocarcinoma, colony 29) cells in PBS into the dorsal surface. The mice, 5 animals per group, received injections of vehicle or vehicle containing compound 11 (5 mg/kg) 3 times per week. Tumor volume was determined by external measurement with an electronic caliper.

From comparison of the growth of the tumors as summarized below, it can be seen that compound 11 significantly inhibited tumor growth.

| Day of Explant | Control tumor (vol. cm$^3$) | compd 11 (tumor vol. cm$^3$) |
| --- | --- | --- |
| 22 | 0.34 | 0.10 |
| 25 | 0.47 | 0.11 |
| 27 | 0.62 | 0.13 |
| 29 | 0.70 | 0.14 |
| 31 | 0.76 | 0.17 |

It will be understood that various details of the invention may be changed without departing from the scope of the invention. Furthermore, the foregoing description is for the purpose of illustration only, and not for the purpose of limitation—the invention being defined by the claims.

What is claimed is:

1. A method for cancer treatment in a warm blooded vertebrate animal, comprising administering to the animal a treatment effective amount sufficient to inhibit cancer of a carboxylic acid secondary amide derivative of a compound, wherein:
    (1) the secondary amide derivative (a) is selective for inhibition of cyclooxygenase-2, and (b) has an indole system, where the indole system has a nitrogen and the indole nitrogen is substituted with para-halobenzoyl, where the halo is selected from the group consisting of fluoro, chloro, and bromo, and
    (2) the compound (a) is a cyclooxygenase inhibitor but is absent selectivity for inhibition of cyclooxygenase-2 and (b) contains a carboxylic acid moiety or a pharmaceutically acceptable salt thereof.

2. The method of claim 1, wherein the cancer treatment is antiangiogenic treatment and the amount sufficient to inhibit cancer is sufficient to inhibit blood cells that feed cancer or blood vessel cells that feed cancer.

3. The method of claim 1, wherein the cancer treatment is antitumor treatment and the amount sufficient to inhibit cancer is sufficient to inhibit tumor growth.

4. The method of claim 3, further including the secondary amide derivative possesses an analgesic, antiinflammatory, or antipyretic property as possessed by the compound and the treatment provides an analgesic, antiinflammatory, or antipyretic effect in the animal absent concomitant administration of another compound for providing such effect.

5. The method of claim 1, wherein the compound is a non-steroidal antiinflammatory drug.

6. The method of claim 5, wherein the non-steroidal antiinflammatory drug is selected from the group consisting of indoles, pharmaceutically acceptable salts thereof, and combinations thereof.

7. The method of claim 5, wherein the non-steroidal antiinflammatory drug is selected from the group consisting of indomethacin, pharmaceutically acceptable salts thereof, and combinations thereof.

8. The method of claim 1, wherein the secondary amide derivative is selected from the group consisting of indomethacin-N-methyl amide, indomethacin-N-ethan-2-ol amide, indomethacin-N-octyl amide, indomethacin-N-nonyl amide, indomethacin-N-(2-methylbenzyl) amide, indomethacin-N-(4-methylbenzyl) amide, indomethacin-N-((R)-,4-dimethylbenzyl) amide, indomethacin-N-((S)-,4-dimethylbenzyl) amide, indomethacin-N-(2-phenethyl) amide, indomethacin-N-(4-fluorophenyl) amide, indomethacin-N-(4-chlorophenyl) amide, indomethacin-N-(4-acetamidophenyl) amide, indomethacin-N-(4-methylmercapto)phenyl amide, indomethacin-N-(3-methylmercaptophenyl) amide, indomethacin-N-(4-methoxyphenyl) amide, indomethacin-N-(3-ethoxyphenyl) amide, indomethacin-N-(3,4,5-trimethoxyphenyl) amide, indomethacin-N-(3-pyridy) amide, indomethacin-N-5-((2-chloro)pyridyl) amide, indomethacin-N-5-((1-ethyl)pyrazolo) amide, indomethacin-N-(3-chloropropyl) amide, indomethacin-N-methoxycarbonylmethyl amide, indomethacin-N-2-(2-L-methoxycarbonylethyl) amide, indomethacin-N-2-(2-D-methoxycarbonylethyl) amide, indomethacin-N-(4-methoxycarbonylbenzyl) amide, indomethacin-N-(4-methoxycarbonylmethylphenyl) amide, indomethacin-N-(2-pyrazinyl) amide, indomethacin-N-2-(4-methylthiazolyl) amide, indomethacin-N-(4-biphenyl) amide, and combinations thereof.

9. The method of claim 1, wherein the treatment effective amount sufficient to inhibit cancer ranges from about 0.5 milligram to about 7.0 milligrams per kilogram of body weight of the animal per day.

10. The method of claim 1, wherein the treatment effective amount sufficient to inhibit cancer ranges from about 1.5 milligrams to about 6.0 milligrams per kilogram of body weight of the animal per day.

11. The method of claim 1, wherein the treatment effective amount sufficient to inhibit cancer ranges from about 2.0 milligrams to about 5.0 milligrams per kilogram of body weight of the animal per day.

* * * * *